United States Patent
Watson et al.

(10) Patent No.: US 9,597,059 B2
(45) Date of Patent: Mar. 21, 2017

(54) CORRECTING FOR UNINTENDED MOTION FOR ULTRASONIC EYE SCANS

(71) Applicants: John D. Watson, Evergreen, CO (US); Andrew K. Levien, Morrison, CO (US)

(72) Inventors: John D. Watson, Evergreen, CO (US); Andrew K. Levien, Morrison, CO (US)

(73) Assignee: ArcScan, Inc., Morrison, CO (US)

( * ) Notice: Subject to any disclaimer, the term of this patent is extended or adjusted under 35 U.S.C. 154(b) by 280 days.

(21) Appl. No.: 13/894,741

(22) Filed: May 15, 2013

(65) Prior Publication Data

US 2013/0310692 A1 Nov. 21, 2013

Related U.S. Application Data

(60) Provisional application No. 61/648,424, filed on May 17, 2012.

(51) Int. Cl.
*A61B 8/10* (2006.01)
*A61B 8/08* (2006.01)
*A61B 8/00* (2006.01)

(52) U.S. Cl.
CPC .............. *A61B 8/5276* (2013.01); *A61B 8/10* (2013.01); *A61B 8/4209* (2013.01);
(Continued)

(58) Field of Classification Search
CPC ....... A61B 8/5276; A61B 8/10; A61B 8/4209; A61B 8/4461; A61B 8/4483; A61B 8/40
(Continued)

(56) References Cited

U.S. PATENT DOCUMENTS

| | | |
|---|---|---|
| 3,371,660 A | 3/1968 | Benson |
| 3,821,891 A | 7/1974 | Collins et al. |

(Continued)

FOREIGN PATENT DOCUMENTS

| | | |
|---|---|---|
| CA | 2295431 | 7/2001 |
| CA | 2299483 | 7/2001 |

(Continued)

OTHER PUBLICATIONS

Binder, "SL-OCT and Ultrasound Support the Need for New Phakic IOL Sizing Strategies," Euro Times, Mar. 2007, p. 11.

(Continued)

*Primary Examiner* — Long V Le
*Assistant Examiner* — Angela M Hoffa
(74) *Attorney, Agent, or Firm* — Sheridan Ross P.C.

(57) ABSTRACT

A device and method are disclosed for detecting and correcting unintended eye movements that may occur during an ultrasound scan by monitoring multiple position tracking sensors, examples being but not limited to ultrasound or optical position sensors. These position tracking sensors are in addition to the ultrasound imaging transducer and are in a fixed position on the scan head so as not to move during the scanning operation. These position tracking sensors can continuously monitor the distance to the cornea or other clearly defined anatomical features of the eye such as the posterior pigment layer of the iris during the movement of the scan head assembly and can provide continuous multi-dimensional correction for any unwanted motion of the eye relative to the scan head that may occur during the ultrasound scan.

16 Claims, 16 Drawing Sheets

(52) U.S. Cl.
CPC .......... *A61B 8/4461* (2013.01); *A61B 8/4483* (2013.01); *A61B 8/40* (2013.01)

(58) Field of Classification Search
USPC ........................................................ 600/424
See application file for complete search history.

(56) References Cited

U.S. PATENT DOCUMENTS

| | | |
|---|---|---|
| 3,997,793 A | 12/1976 | Rogers et al. |
| 4,114,214 A | 9/1978 | VonHeck |
| 4,154,114 A | 5/1979 | Katz |
| 4,183,249 A | 1/1980 | Anderson |
| 4,206,763 A | 6/1980 | Pedersen |
| 4,227,780 A | 10/1980 | Ohta et al. |
| 4,245,250 A | 1/1981 | Tiemann |
| 4,347,213 A | 8/1982 | Rogers |
| 4,484,569 A | 11/1984 | Driller et al. |
| 4,493,877 A | 1/1985 | Burnett |
| 4,550,607 A | 11/1985 | Maslak et al. |
| 4,564,018 A | 1/1986 | Hutchison et al. |
| 4,807,634 A | 2/1989 | Enjoji et al. |
| 4,815,047 A | 3/1989 | Hart |
| 4,817,432 A | 4/1989 | Wallace et al. |
| 4,823,801 A | 4/1989 | Sakane |
| 4,858,124 A | 8/1989 | Lizzi et al. |
| 4,858,613 A | 8/1989 | Fry et al. |
| 4,930,512 A | 6/1990 | Henriksen et al. |
| 4,932,414 A | 6/1990 | Coleman et al. |
| 5,029,587 A | 7/1991 | Baba et al. |
| 5,079,786 A | 1/1992 | Rojas |
| 5,103,517 A | 4/1992 | Krouskop |
| 5,116,114 A | 5/1992 | Nakamura et al. |
| 5,152,746 A | 10/1992 | Atkinson et al. |
| 5,293,871 A | 3/1994 | Reinstein et al. |
| 5,331,962 A | 7/1994 | Coleman et al. |
| 5,369,454 A | 11/1994 | Reinstein et al. |
| 5,387,180 A | 2/1995 | Lehmer |
| 5,460,179 A | 10/1995 | Okunuki et al. |
| 5,474,070 A | 12/1995 | Ophir et al. |
| 5,487,388 A | 1/1996 | Rello et al. |
| 5,551,432 A | 9/1996 | Iezzi |
| 5,556,169 A | 9/1996 | Parrish et al. |
| 5,614,099 A | 3/1997 | Hirose et al. |
| 5,626,150 A | 5/1997 | Johnson et al. |
| 5,626,594 A | 5/1997 | Smith |
| 5,671,739 A * | 9/1997 | Darrow et al. ............... 600/424 |
| 5,776,068 A | 7/1998 | Silverman et al. |
| 5,826,583 A | 10/1998 | Wood |
| 5,832,550 A | 11/1998 | Hauger et al. |
| 5,855,207 A | 1/1999 | Moenning et al. |
| 5,906,205 A | 5/1999 | Hiebert |
| 5,966,763 A | 10/1999 | Thomas et al. |
| 5,971,006 A | 10/1999 | Seigerschmidt |
| 6,053,613 A | 4/2000 | Wei et al. |
| 6,145,143 A | 11/2000 | Hicks et al. |
| 6,154,204 A | 11/2000 | Thompson et al. |
| 6,198,956 B1 | 3/2001 | Dunne |
| 6,315,727 B1 | 11/2001 | Coleman et al. |
| 6,318,372 B1 | 11/2001 | Hiebert |
| 6,334,227 B1 | 1/2002 | Larger |
| 6,374,439 B2 | 4/2002 | Heimbrock et al. |
| 6,451,008 B1 * | 9/2002 | Frey et al. ...................... 606/10 |
| 6,460,207 B1 | 10/2002 | Papay et al. |
| 6,487,447 B1 | 11/2002 | Weimann et al. |
| 6,491,637 B2 | 12/2002 | Foster et al. |
| 6,574,813 B2 | 6/2003 | Bolden et al. |
| 6,629,929 B1 | 10/2003 | Jago et al. |
| 6,684,433 B2 | 2/2004 | Giori et al. |
| 6,837,855 B1 | 1/2005 | Puech |
| 6,868,569 B2 | 3/2005 | VanSteenburg |
| 6,887,203 B2 | 5/2005 | Phillips et al. |
| 6,923,767 B2 | 8/2005 | Saied et al. |
| 6,981,417 B1 | 1/2006 | Oravecz |
| 7,048,690 B2 | 5/2006 | Coleman et al. |
| 7,168,116 B2 | 1/2007 | Reger et al. |
| 7,237,898 B1 | 7/2007 | Hohla |
| 7,356,905 B2 | 4/2008 | Ketterling et al. |
| 7,451,507 B2 | 11/2008 | Brinkerhoff et al. |
| 7,454,024 B2 | 11/2008 | Ketterling et al. |
| 7,474,041 B2 | 1/2009 | Ketterling et al. |
| 7,480,058 B2 | 1/2009 | Zhao et al. |
| 7,611,507 B2 | 11/2009 | Raksi et al. |
| 7,708,342 B2 | 5/2010 | Leach |
| 7,920,909 B2 * | 4/2011 | Lyon et al. ................... 600/407 |
| 8,064,989 B2 | 11/2011 | Brown et al. |
| 8,068,647 B2 * | 11/2011 | Lin .................................. 382/128 |
| 8,115,935 B2 | 2/2012 | Everett et al. |
| 8,317,709 B2 | 11/2012 | Eilers et al. |
| 8,496,588 B2 | 7/2013 | Eilers et al. |
| 8,510,883 B2 | 8/2013 | Eilers et al. |
| 8,732,878 B2 | 5/2014 | Eilers et al. |
| 8,758,252 B2 * | 6/2014 | Eilers et al. .................. 600/459 |
| 8,824,743 B2 * | 9/2014 | Daigle .......................... 382/107 |
| 2002/0085173 A1 | 7/2002 | Schippert et al. |
| 2002/0143252 A1 | 10/2002 | Dunne et al. |
| 2003/0004416 A1 | 1/2003 | Phillips et al. |
| 2003/0142269 A1 | 7/2003 | Cumming |
| 2004/0200754 A1 | 10/2004 | Hagemeier |
| 2004/0220478 A1 | 11/2004 | Wallace et al. |
| 2005/0120479 A1 | 6/2005 | Habashi et al. |
| 2006/0029525 A1 | 2/2006 | Laugharn, Jr. et al. |
| 2006/0241533 A1 | 10/2006 | Geller |
| 2006/0288487 A1 | 12/2006 | Roleder et al. |
| 2007/0014445 A1 * | 1/2007 | Lin .................................. 382/128 |
| 2007/0051362 A1 | 3/2007 | Sullivan et al. |
| 2007/0083995 A1 | 4/2007 | Purdy et al. |
| 2007/0239030 A1 | 10/2007 | Prager et al. |
| 2007/0276233 A1 | 11/2007 | Besson et al. |
| 2008/0097214 A1 | 4/2008 | Meyers et al. |
| 2008/0146939 A1 | 6/2008 | McMorrow et al. |
| 2009/0088623 A1 | 4/2009 | Vortman et al. |
| 2009/0192389 A1 * | 7/2009 | Eilers et al. .................. 600/459 |
| 2009/0234369 A1 | 9/2009 | Bax et al. |
| 2009/0318758 A1 | 12/2009 | Farr et al. |
| 2010/0004538 A1 | 1/2010 | Eilers et al. |
| 2010/0031448 A1 | 2/2010 | Hijlkema |
| 2010/0217125 A1 | 8/2010 | Kadokura et al. |
| 2010/0229306 A1 | 9/2010 | Reeder et al. |
| 2010/0249562 A1 | 9/2010 | Zhang |
| 2010/0321697 A1 | 12/2010 | Zheng et al. |
| 2011/0172511 A1 | 7/2011 | Schmitt et al. |
| 2012/0320368 A1 | 12/2012 | Jiao |
| 2013/0072755 A1 | 3/2013 | Papania et al. |
| 2013/0085370 A1 | 4/2013 | Friedman |
| 2013/0144171 A1 | 6/2013 | Watson |
| 2013/0237826 A1 * | 9/2013 | Levien .......................... 600/448 |
| 2014/0009741 A1 * | 1/2014 | Levien et al. ................. 351/206 |
| 2014/0249422 A1 | 9/2014 | Eilers et al. |
| 2015/0238166 A1 | 8/2015 | Heath et al. |

FOREIGN PATENT DOCUMENTS

| | | |
|---|---|---|
| CA | 2395203 | 7/2001 |
| CA | 2409234 | 4/2004 |
| JP | 2006-149001 | 6/2006 |

OTHER PUBLICATIONS

Coleman et al., "Ultrasonography of the Eye and Orbit," Second Edition, published by Lippincott Williams & Wilkins, 2006, pp. 1-186.

Izatt et al., "Theory of Optical Coherence Tomography," Chap. 2 of "Optical Coherence Tomography Technology and Applications," Drexler and Fujimoto eds, ISBN:978-3-540-77549-2, 2008, pp. 47-72.

Ketterling, "Design and Fabrication of a 40-MHz Annular Array Transducer," IEEE Transactions on Ultrasonics, Ferroelectrics, and Frequency Control, Apr. 2005, vol. 52, No. 4, pp. 672-681.

Ketterling, "Operational Verification of a 40-MHz Annular Array Transducer," IEEE Transactions on Ultrasonics, Ferroelectrics, and Frequency Control, Mar. 2006, vol. 53, No. 3, pp. 623-630.

(56) References Cited

OTHER PUBLICATIONS

Mamou, "Chirp-Coded Excitation Imaging With a High-Frequency Ultrasound Annular Array," IEEE Transactions on Ultrasonics, Ferroelectrics, and Frequency Control, Feb. 2008, vol. 55, No. 2, pp. 508-513.
Pinero et al., "Equivalence, Differences Identified in Biometric Analysis," Cataract & Refractive Surgery Today, Mar. 2008, vol. 3, No. 12, pp. 46-49.
Reinstein et al., "Repeatability of Layered Corneal Pachymetry with the Artemis Very High Frequency Digital Ultrasound Arc-Scanner," J. Refractive Surg., vol. 26(9), 2009, original article, 6 pages.
Reinstein, "Subsurface Screening for Keratoconus—Accurate Measurements of the Epithelial and Stromal Layers Aid in Diagnosis," Cataract and Refractive Surgery Today, May 2007, pp. 88-89.
Roholt, "Sizing the Visian ICL," Cataract and Refractive Surgery Today, May 2007, p. 50.
Silverman et al., "Improved System for Sonographic Imaging and Biometry of the Cornea," J. Ultrasound Med., 1997, vol. 16, pp. 117-124.
Angelson et al. "Which transducer array is best?" European Journal of Ultrasound, 1995, vol. 2., pp. 151-164.

\* cited by examiner

CORRECTING FOR UNINTENDED MOTION FOR ULTRASONIC EYE SCANS

CROSS-REFERENCE TO RELATED APPLICATIONS

This application claims the benefits, under 35 U.S.C. §119(e), of U.S. Provisional Application Ser. No. 61/648,424 entitled "Correcting for Unintended Motion for Ultrasonic Eye Scans" filed May 17, 2012 which is incorporated herein by reference.

FIELD

The present disclosure relates in general to a device and methods of accounting for unintended eye movements during an ultrasound scan set and includes optical and ultrasound methods of tracking specific eye components.

BACKGROUND

Except for on-axis measurements, dimensions and locations of eye components behind the iris cannot be fully determined by optical means. Ultrasonic imaging in the frequency range of about 5 MHz to about 80 MHz can be applied to make accurate and precise measurements of structures of the eye, such as, for example, the cornea and lens.

An ultrasound scanning apparatus is described in the following patent applications, all of which are incorporated by reference:
1. U.S. patent application Ser. No. 12/347,674 entitled "Components for an Ultrasonic Arc Scanning Apparatus" filed Dec. 31, 2008;
2. U.S. patent application Ser. No. 12/418,392 entitled "Procedures for an Ultrasonic Arc Scanning Apparatus" filed Apr. 3, 2009;
3. U.S. patent application Ser. No. 12/475,322 entitled "Compound Scanning Head for an Ultrasonic Scanning Apparatus" filed May 29, 2009;
4. U.S. patent application Ser. No. 12/638,661 entitled "Alignment and Imaging of an Eye with an Ultrasonic Scanner" filed Dec. 15, 2009;
5. U.S. patent application Ser. No. 12/754,444 entitled "Method of Positioning a Patient for Medical Procedures" filed Apr. 5, 2010; and
6. U.S. patent application Ser. No. 13/684,699 entitled "Alignment and Imaging of an Eye with an Ultrasonic Scanner" filed Nov. 26, 2012.

Ultrasonic imaging has been used in corneal procedures such as LASIK to make accurate and precise images and maps of cornea thickness which include epithelial thickness, Bowman's layer and images of LASIK flaps. These images have an A-scan resolution of about 5 microns.

New procedures such as implantation of accommodative lenses may provide nearly perfect vision without spectacles or contact lenses. Implantation of accommodative lenses requires precision measurements of, for example, the position and width of the natural lens for successful lens powering and implantation. Ultrasonic imaging can be used to provide the required accurate images of the natural lens especially where the zonules attach the lens to the ciliary body which is well off-axis and behind the iris and therefore not accessible to optical imaging. Other new procedures such as implantation of stents in or near the suprachoroid may provide part or all of a treatment for glaucoma. Ultrasonic imaging can be used to provide the required accurate images in the corner of the eye between the sclera and the iris (in the suprachoroidal space) which is well off-axis and relatively inaccessible to optical imaging.

Such measurements provide ophthalmic researchers with valuable information that can be used 1) in the design of accommodative lenses, 2) provide ophthalmic surgeons with valuable information that can be used to guide various surgical procedures performed on the lens, 3) in the design of glaucoma stents, 4) provide ophthalmic surgeons with valuable information that can be used to guide placement of stents for treatment of glaucoma.

Recent advances in ultrasonic imaging have allowed images of substantially the entire lens capsule to be made. This has opened up the ability of diagnostic devices to assist in both research of lens implantation devices and strategies, and to planning, executing and follow-up diagnostics for corrective lens surgery including specialty procedures such as glaucoma and cataract treatments as well as implantation of clear intraocular lenses including accommodative lens.

The use of ultrasonic imaging of important features of the eye for lens implantation is discussed, for example, in U.S. Pat. No. 7,048,690. This patent does not include techniques for imaging the posterior surface of the lens capsule and so cannot be used to compute the volume of a lens capsule. Means for obtaining a full image of the lens capsule are disclosed in U.S. patent application Ser. No. 12/475,322 and U.S. patent application Ser. No. 12/638,661.

An ultrasonic scan of the eye may include one or more rapid B-scans (each B-scan formed from a plurality of A-scans) at each of several meridians (typically about 3 to about 12 meridians) and these may be combined automatically to form a comprehensive image of the anterior segment. Therefore it is necessary to rapidly scan a patient to reduce the possibility of patient eye motion during a scan session. Further, it may be necessary to re-scan a patient at a later time in order to determine if changes in features or dimensions has occurred.

The speed of transducer motion in an precision scanning device such as described, for example, in U.S. patent application Ser. No. 12/638,661, is limited because its movement is in a bath of water and excessive speed of motion of the transducer and its carriage can result in vibration of the entire instrument. In practice, a set of ultrasound scans can be carried out in about 1 to about 3 minutes from the time the patient's eye is immersed in water to the time the water is drained from the eyepiece. The actual scanning process itself can be carried out in several tens of seconds, after the operator or automated software completes the process of centration (centration means aligning the center of curvature of the scanning transducer in space with the center of curvature of the eye component of interest such that rays from the transducer pass substantially through both centers of curvature). As is often the case, the patient may move his or her head slightly or may move his or her eye in its socket during this time. In some cases, the patient's heart beat can be detected as a slight blurring of the images. If patient movements are large, the scan set can always be repeated.

It is also important to compensate for unintended patient head or eye motion because a scan of the anterior segment scan or lens capsule scan is typically made by overlaying two or three separate scans (such as an arcuate scan followed by two linear scans, also described in U.S. patent application Ser. No. 12/638,661.

There remains, therefore, a need for methods that can be used track unintended movements of the eye during scanning to provide a reliable reference for multiple scans in a scanning session. Additionally, these methods are required to track a reference point in an eye during scanning and to locate this reference point for scanning sessions conducted at a later time.

SUMMARY

These and other needs are addressed by the present disclosure. The various embodiments and configurations of the present disclosure are directed generally to a device and methods of detecting and recording unintended eye movement that may occur during an ultrasound scan by monitoring multiple position tracking sensors, examples being but not limited to ultrasound or optical position sensors. These position tracking sensors are in addition to the ultrasound imaging transducer and are in a fixed position on the scan head positioning mechanism so as not to move during the scanning operation. These position tracking sensors will continuously monitor the distance to the cornea or other clearly defined anatomical features of the eye such as, for example, the cornea, the posterior apex of the lens surface, the anterior apex of the lens surface, the inside edge of the pupil and/or the posterior pigment layer of the iris. These fiducial points and surfaces can be detected during the movement of the scan head and provide continuous multidimensional correction for any unwanted motion of the eye that may occur during the ultrasound scan, these motions being relative to the positioning mechanism head which is commonly fixed during the scanning process.

In one embodiment, an ultrasonic scanning system is disclosed, the system comprising: an instrument body configured to engage a patient and position the patient's head and an eye; and a positioner assembly connected to the instrument body, the positioner assembly comprising a scan head assembly, the scan head assembly comprising at least one position sensor, the at least one position sensor fixed relative to the positioner assembly, the scan head assembly further comprising at least one guide track, at least one transducer carriage and at least one ultrasonic transducer; wherein the at least one transducer carriage moves along the at least one guide track; wherein the at least one ultrasound transducer emits and receives an ultrasound pulse reflected from one or more components of the patient's eye when the patient's head is engaged with the instrument body; and wherein at least one position sensor measures the position of the patient's eye.

In another embodiment, a method is disclosed for forming an ultrasound image of a patient's eye corrected for eye movement, the method comprising: (a) positioning a patient to engage an ultrasonic scanning system, the system comprising: an instrument body configured to engage a patient and position the patient's head and an eye; and a positioner assembly connected to the instrument body, the positioner assembly comprising a scan head assembly, the scan head assembly comprising at least one position sensor, the at least one position sensor fixed relative to the positioner assembly, the scan head assembly further comprising at least one guide track, at least one transducer carriage and at least one ultrasonic transducer and wherein the at least one transducer carriage moves along the at least one guide track; (b) moving the at least one ultrasound transducer along the at least one guide track while emitting and receiving ultrasound pulses reflected from one or more components of the patient's eye; (c) measuring the position of the patient's eye by the at least one position sensor; (d) recording the ultrasound pulses and the measurements of the position of the patient's eye on a non-transitory computer readable medium; and (e) altering the recordings of the ultrasound pulses by use of the measurements of the position of the patient's eye to correct for movement of the patient's eye.

In yet another embodiment, an ultrasonic scanning device is disclosed, the device comprising: an instrument body configured to engage and position a patient's eye comprising an eyepiece and a headrest, the eyepiece and the headrest urging positional fixing of an eye socket of the patient's eye such that the eye socket of the patient's eye is substantially fixed relative to the instrument body; and a positioner assembly connected to the instrument body, the positioned assembly comprising a scan head assembly, the scan head assembly comprising at least one position sensor, the at least one position sensor fixed relative to the positioner assembly and measuring the eye position relative to at least one of the eye socket, the instrument body, the positioner assembly and an eye fiducial, the scan head assembly further comprising at least one guide track, at least one transducer carriage and at least one ultrasonic transducer; wherein the at least one transducer carriage is automatically moveable along the at least one guide track under computer control; wherein the ultrasound transducer emits and receives an ultrasound pulse reflected from one or more components of the patient's eye when the patient is engaged with the instrument body; wherein at least one position sensor measures the position of the patient's eye; wherein the ultrasound pulses and the measurements of the position of the patient's eye are recorded on a non-transitory computer readable medium; and wherein the measurements of the position of the patient's eye are used to alter the recordings of the ultrasound pulses to account for movement of the patient's eye.

The above-described embodiments and configurations are neither complete nor exhaustive. As will be appreciated, other embodiments of the disclosure are possible utilizing, alone or in combination, one or more of the features set forth above or described in detail below.

The following definitions are used herein:

The phrases at least one, one or more, and/or are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

An acoustically reflective surface or interface is a surface or interface that has sufficient acoustic impedance difference across the interface to cause a measurable reflected acoustic signal. A specular surface is typically a very strong acoustically reflective surface.

Animate means of or relating to animal life as opposed to plant life.

Anterior means situated at the front part of a structure; anterior is the opposite of posterior.

An A-scan is a representation of a rectified, filtered reflected acoustic signal as a function of time, received by an ultrasonic transducer from acoustic pulses originally emitted by the ultrasonic transducer from a known fixed position relative to an eye component.

An accommodative lens, also known as a presbyopic lens or presby lens, is an artificial intraocular lens that changes its focal distance in response to contraction of the ciliary body. When successfully implanted, an accommodative lens reverses presbyopia, the inability of the eye to change its focal distance from far to near.

Accuracy as used herein means free from error.

Aligning means positioning the acoustic transducer accurately and reproducibly in all three dimensions of space with respect to a feature of the eye component of interest (such as the center of the pupil, center of curvature or boundary of the cornea, lens, retina, etcetera).

The anterior chamber comprises the region of the eye from the cornea to the iris.

The anterior segment comprises the region of the eye from the cornea to the back of the lens.

An aperture refers to the ultrasonic transducer face which may be planar but is commonly shaped as a concave surface so as to form a focal point at a desired location in front of the transducer face.

An arc scanner is an ultrasound scanning device utilizing a transducer that both sends and receives pulses as it moves along an arcuate guide track, which guide track has a center of curvature whose position can be moved to scan different curved surfaces.

Arc scanning transducer center of curvature is the same as the center of curvature of the arc scanning guide.

Automatic refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Auto-centering means automatically, typically under computer control, causing centration of the arc scanning transducer with the eye component of interest.

A B-scan is a processed representation of A-scan data by either or both of converting it from a time to a distance using acoustic velocities and by using grayscales, which correspond to A-scan amplitudes, to highlight the features along the A-scan time history trace (the latter also referred to as an A-scan vector).

A canthus is the angular junction of the eyelids at either corner of the eye where the upper and lower eyelids meet.

Center of rotation of the eye, there is a point within the eyeball that is more or less fixed relative to the orbit when the eye rotates in its orbit. It is considered that the center of rotation of an emmetropic eye (that is, a normal eye with about 20/20 vision) lies on the line of sight of the eye about 13.5 mm behind the anterior pole of the cornea when the line of sight of the eye is perpendicular to both the base line and the frontal plane.

Centration means substantially aligning the center of curvature of the arc scanning transducer in all three dimensions of space with the center of curvature of the eye component of interest (such as the cornea, pupil, lens, retina, etcetera) such that rays from the transducer pass through both centers of curvature. A special case is when both centers of curvature are coincident.

The ciliary body is the circumferential tissue inside the eye composed of the ciliary muscle and ciliary processes. There are three sets of ciliary muscles in the eye, the longitudinal, radial, and circular muscles. They are near the front of the eye, above and below the lens. They are attached to the lens by connective tissue called the zonule of Zinn, and are responsible for shaping the lens to focus light on the retina. When the ciliary muscle relaxes, it flattens the lens, generally improving the focus for farther objects. When it contracts, the lens becomes more convex, generally improving the focus for closer objects.

Coronal means of or relating to the frontal plane that passes through the long axis of a body. With respect to the eye or the lens, this would be the equatorial plane of the lens which also approximately passes through the nasal canthus and temporal canthus of the eye.

Fiducial means a reference, marker or datum in the field of view of an imaging device.

Fixation means having the patient focus an eye on an optical target such that the eye's optical axis is in a known spatial relationship with the optical target. In fixation, the light source is axially aligned in the arc plane with the light source in the center of the arc so as to obtain maximum signal strength such that moving away from the center of the arc in either direction results in signal strength diminishing equally in either direction away from the center.

A guide is an apparatus for directing the motion of another apparatus.

Haptics are little protrusions extending from the outer diameter of some types of artificial lenses. These haptics fix the position of the lens to the ciliary body by protruding into the ciliary sulcus. In the case of accommodative lenses, the haptics enable the lens to accommodate in response to the action of the ciliary body.

The home position of the imaging ultrasound transducer is its position during the registration process.

An imaging ultrasound transducer is the device that is responsible for creating the outgoing ultrasound pulse and detecting the reflected ultrasound signal that is used for creating the A-Scans and B-Scans.

An intraocular lens is an artificial lens that is implanted in the eye to take the place of the natural lens.

LASIK is a procedure performed on the cornea for correcting refractive errors, such as myopia, hyperopia, and astigmatism. Commonly, an excimer laser selectively removes tissue from the inside of the cornea, after it is exposed, by cutting a thin flap, so as to reshape the external shape of the cornea.

As used herein, a meridian is a 2-dimensional plane section through the approximate center of a 3-dimensional eye and its angle is commonly expressed relative to a horizon defined by the nasal canthus and temporal canthus of the eye.

The natural lens (also known as the aquula or crystalline lens) is a transparent, biconvex structure in the eye that, along with the cornea, helps to refract light to be focused on the retina. The lens, by changing shape, functions to change the focal distance of the eye so that it can focus on objects at various distances, thus allowing a sharp real image of the object of interest to be formed on the retina. This adjustment of the lens is known as accommodation. The lens is located in the anterior segment of the eye behind the iris. The lens is suspended in place by the zonular fibers, which attach to the lens near its equatorial line and connect the lens to the ciliary body. The lens has an ellipsoid, biconvex shape whose size and shape can change due to accommodation and due to growth during aging. The lens is comprised of three main parts: namely the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are generally found only on the anterior side of the lens.

Ocular means having to do with the eye or eyeball.

Ophthalmology means the branch of medicine that deals with the eye.

Optical as used herein refers to processes that use light rays.

The optical axis of the eye is a straight line through the centers of curvature of the refracting surfaces of an eye (the anterior and posterior surfaces of the cornea and lens).

As used herein, the orbit of the eye is the cavity or socket of the skull in which the eye and its appendages are situated. In the adult human, the volume of the orbit is about 30 ml, of which the eye occupies about 6.5 ml.

Organ means a differentiated structure (as a heart, kidney or eye) consisting of cells and tissues and performing some specific function in an organism.

Pachymetery or corneal pachymetery is technically referred to as Time Domain Reflectometry ultrasound. A pulse of ultrasonic energy is sent toward the cornea and the time spacing of the returning echoes are used to arrive at corneal thickness.

Phakic intraocular lenses, or phakic lenses, are lenses made of plastic or silicone that are implanted into the eye permanently to reduce a person's need for glasses or contact lenses. Phakic refers to the fact that the lens is implanted into the eye without removing the eye's natural lens. During phakic lens implantation surgery, a small incision is normally made in the front of the eye. The phakic lens is inserted through the incision and placed just in front of or just behind the iris.

Positioner means the mechanism that positions a scan head relative to a selected part of an eye. In the present disclosure, the positioner can move back and forth along the x, y or z axes and rotate in the β direction about the z-axis. Normally the positioner does not move during a scan, only the scan head moves. In certain operations, such as measuring the thickness of a region, the positioner may move during a scan.

Position tracking sensors are a set of position sensors whose sole purpose is to monitor the movement of the eye or any other anatomical feature during the imaging scan so as to remove unwanted movement of the feature.

Posterior means situated at the back part of a structure; posterior is the opposite of anterior.

The posterior chamber comprises the region of the eye from the back of the iris to the front of the lens.

The posterior segment comprises the region of the eye from the back of the lens to the rear of the eye comprising the retina and optical nerve.

Precise as used herein means sharply defined.

Precision means how close in value successive measurements fall when attempting to repeat the same measurement between two detectable features in the image field. In a normal distribution precision is characterized by the standard deviation of the set of repeated measurements. Precision is very similar to the definition of repeatability.

Presbyiopia is typically caused by a loss of elasticity of the natural lens inside the eye. This occurs as part of the ageing process and, although it cannot be 'cured', it can be corrected by wearing glasses or implanting an artificial lens.

The pulse transit time across a region of the eye is the time it takes a sound pulse to traverse the region.

Purkinje images are reflections of objects from structure of the eye. There are at least four Purkinje images that are visible on looking at an eye. The first Purkinje image (P1) is the reflection from the outer surface of the cornea. The second Purkinje image (P2) is the reflection from the inner surface of the cornea. The third Purkinje image (P3) is the reflection from the outer (anterior) surface of the lens. The fourth Purkinje image (P4) is the reflection from the inner (posterior) surface of the lens. Unlike the others, P4 is an inverted image. The first and fourth Purkinje images are used by some eye trackers, devices to measure the position of an eye. Purkinje images are named after Czech anatomist Jan Evangelista Purkyně (1787-1869).

Refractive means anything pertaining to the focusing of light rays by the various components of the eye, principally the cornea and lens.

Registration as used herein means aligning.

Saccades are quick, simultaneous rotations of both eyes in the same direction involving a succession of discontinuous individual rotations of the eye orbit in the eye socket. These rapid motions can be on the order of 20 degrees of rotation with a maximum velocity of 200 degrees/sec and are a part of normal eyesight.

Scan head means the mechanism that comprises the ultrasound transducer, the transducer holder and carriage as well as any guide tracks that allow the transducer to be moved relative to the positioner. Guide tracks may be linear, arcuate or any other appropriate geometry. The guide tracks may be rigid or flexible. Normally, only the scan head is moved during a scan.

Sector scanner is an ultrasonic scanner that sweeps a sector like a radar. The swept area is pie-shaped with its central point typically located near the face of the ultrasound transducer.

A specular surface means a mirror-like surface that reflects either optical or acoustic waves. For example, an ultrasound beam emanating from a transducer will be reflected directly back to that transducer when the beam is aligned perpendicular to a specular surface.

The ciliary sulcus is the groove between the iris and ciliary body. The scleral sulcus is a slight groove at the junction of the sclera and cornea.

The suprachoroid lies between the choroid and the sclera and is composed of closely packed layers of long pigmented processes derived from each tissue.

The suprachoroidal space is a potential space providing a pathway for uveoscleral outflow and becomes an actual space in choroidal detachment. The hydrostatic pressure in the suprachoroidal space is an important parameter for understanding intraocular fluid dynamics and the mechanism of choroidal detachment.

Tissue means an aggregate of cells usually of a particular kind together with their intercellular substance that form one of the structural materials of a plant or an animal and that in animals include connective tissue, epithelium, muscle tissue, and nerve tissue.

A track or guide track is an apparatus along which another apparatus moves.

Ultrasonic means sound that is above the human ear's upper frequency limit. When used for imaging an object like the eye, the sound passes through a liquid medium, and its frequency is many orders of magnitude greater than can be detected by the human ear. For high-resolution acoustic imaging in the eye, the frequency is typically in the approximate range of about 5 to about 80 MHz.

A vector refers to a single acoustic pulse and its multiple reflections from various eye components. An A-scan is a representation of this data whose amplitude is typically rectified.

The visual axis of the eye is the line joining the object of interest and the fovea and which passes through the nodal points of the eye.

Zonules are tension-able ligaments extending from near the outer diameter of the crystalline lens. The zonules attach the lens to the ciliary body which allows the lens to accommodate in response to the action of the ciliary muscle.

BRIEF DESCRIPTION OF THE DRAWINGS

The present disclosure may take form in various components and arrangements of components, and in various steps and arrangements of steps. The drawings are only for purposes of illustrating the preferred embodiments and are not to be construed as limiting the disclosure. In the drawings, like reference numerals refer to like or analogous components throughout the several views.

DETAILED DESCRIPTION

Figure 1:
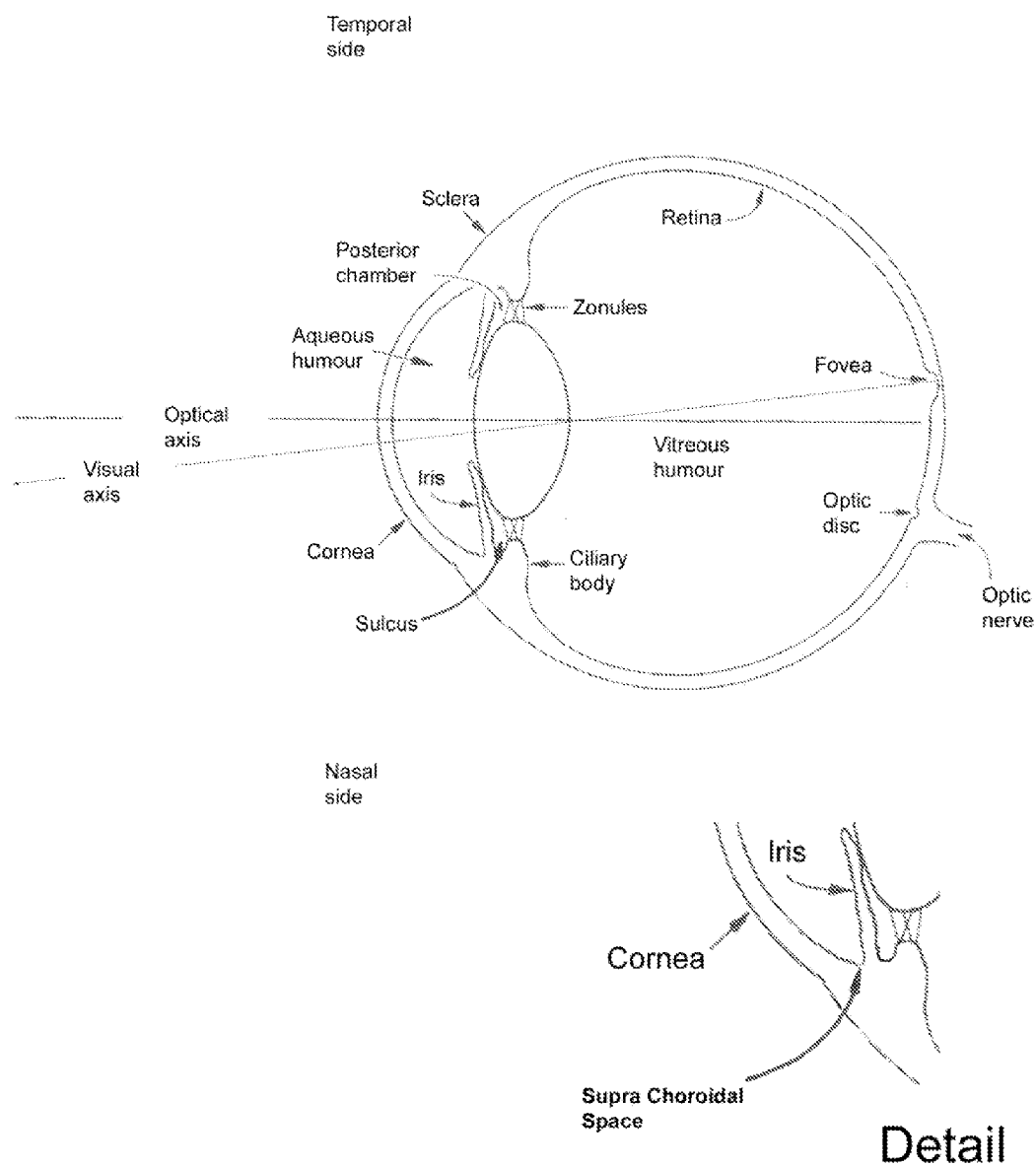
FIG. 1 is schematic of the main elements of a human eye.

Saccades are quick, simultaneous rotations of both eyes in the same direction involving a succession of discontinuous individual rotations of the eye orbit in the eye socket. These rapid motions can be on the order of 20 degrees of rotation with a maximum velocity of 200 degrees/sec and are a part of normal eyesight. The center of rotation of these rotations is approximately 13 degrees posterior to the apex of the cornea along the optical axis of the eye. Despite the utilization of a fixation target within the device as described in prior patents referenced herein, these saccadic movements may occur from time to time during a scan.

It is noted that a positioner (also referred to as a or positioning mechanism or positioning assembly) means the mechanism that positions a scan head relative to a selected part of an eye. Normally the positioner does not move during a scan, only the scan head moves. In certain operations (such as measuring the thickness and speed of sound of an eye component as described in U.S. patent application Ser. No. 13/684,699), the positioner may move during a scan, the positioner may move during a scan. A scan head means the mechanism that comprises the ultrasound transducer, the transducer holder and carriage as well as any guide tracks that allow the transducer to be moved relative to the positioner. Guide tracks may be linear, arcuate or any other appropriate geometry.

Prior to any scan, the scan head is positioned and registered assuring that in the case of the eye, the imaging ultrasound transducer is aligned with the approximate center of curvature of the cornea and is also approximately orthogonal to the cornea surface as has been taught in prior art. Three or fewer additional position tracking sensors are placed in proximity to the imaging ultrasound transducer in its home position but not on the moveable part of the scan head, instead fixed to the stationary portion of the scan head that is rigidly attached to the positioner. The minimum number of position tracking sensors will be related to how many axes of motion that are desired from the eye during the scan. The alignment of these position tracking sensors is such that they measure the distance to anatomical eye feature of interest in close proximity to where the imaging ultrasound transducer also derives its image in its home position.

Prior to any scan head movement, a set of distance measurements are taken from the position tracking sensors as the ultrasound imaging transducer is in its home position and in several others positions about the home position effected by known movement of the positioner or alternatively by having a plurality of fixation targets and making measurements to the anatomical feature of interest as the eye fixates on each of the fixation targets. This sequence of movements is to calibrate for the unique anatomy and eye movement of each patient. This sequence of preliminary measurements is defined as the tracking calibration sequence.

Similarly the position sensors could also measure change in amplitude of reflected signal as another means to track eye movement as any movement of the eye will reflect the position tracking sensor beam (whether ultrasound or optical) in a different direction away from the original reflection causing a change in amplitude of the reflected signal.

Once the tracking calibration sequence is complete the scan head movement can commence. During the scan head movement, the fixed position tracking sensors can be monitored at intermediate times during the scan to provide continuous tracking of eye movement.

This tracking information can be used in several different ways:

1) cause the positioning mechanism to move in response to compensate for patient eye motion during the scan head movement;

2) correct the image for this motion in real-time or near real-time or later during post-processing after the scan is complete;

3) warn the patient and/or the operator of patient eye movement above one or more selectable thresholds; and/or 4) instruct the scanning machine to automatically abort the scan if the detected movement is above a predetermined threshold and have the instrument automatically redo the entire scan sequence (e.g. in the case of a multi-meridian scan) or redo only that individual scan on which the motion was detected and then continue scanning.

Another embodiment does not use any tracking sensors and relies solely on the B-Scan image itself when a regular anatomy, such as the cornea is being scanned. For example, the surface of the cornea is a very clearly defined and regular geometry (approximately an elliptical or almost spherical surface). In a normal B-Scan of the cornea produced by an ultrasound scanner, there would be relatively small variations in the distance from the imaging scan sensor to the surface of the cornea. However, in the case of a saccadic eye movement, the change in this distance over a number of individual A-Scans may be quite large compared to the small changes that would be expected in a normal scan. This large distance change would be a clear indication of a saccadic movement and basis for rejection of the scan and treated similarly as tracking information use 4) above.

An ultra sound scanning apparatus as described in U.S. patent application Ser. No. 12/638,661 is comprised of a positioning mechanism and a scan head. The positioning mechanism has x, y, z and beta (rotation about its axis) positioning mechanisms which make it possible to position the scan head relative to the eye component of interest. This operation is carried out while the patient's eye is positioned in contact with an eyepiece attached to the scanner and while the patient's head is fixed relative to the scanner by a head rest. Once the positioning mechanism is set, the only moving part relative to the eye component of interest is the scan head. The scan head may be comprised of only an arcuate guide track which is typically used to produce an ultrasound scan of the cornea or much of the anterior segment of an eye. The scan head may also be moved in a combination of linear and arcuate motions to produce an ultrasound scan of the entire anterior segment including much of the posterior surface of the lens. The movement of the scan head relative to the positioning mechanism is precisely known at all times by a system of magnetic encoder strips.

The movement of the scan head relative to the eye component of interest is therefore known with precision and accuracy as long as the patient does not move their eye during the scan. A single scan can take less than a second. A sequence of scans can take tens of seconds. A patience eye can move significantly even during a single scan, thus degrading the precision and accuracy of the scan. The usual procedure, when this occurs, is to re-scan the patient. It is the intent of the present disclosure to disclose a device and method of tracking any movement of the patient's eye, relative to the positioning mechanism, during a scan so that actions can be taken as described above.

One of the devices and/or methods disclosed herein uses ultrasound transducers that are mounted on the base plate of the scan head which is rigidly connected to a positioning mechanism (which is typically not intended to move during scans). Optical sensors may also be used for this tracking function.

These position tracking sensors are in addition to the ultrasound imaging transducer and are in a fixed position on the stationary portion of the positioning mechanism so as not to move relative to the patient's eye during the scanning operation. For example, these position tracking sensors will monitor the distance to the front surface of the cornea, pupil, lens or posterior surface of the iris continuously during the movement of the scan head and provide continuous multi-dimensional correction for any unwanted motion of the eye relative to the positioning mechanism that may occur during the ultrasound scan.

Prior to any scan, the scan head is registered assuring that in the case of the eye the imaging ultrasound transducer is aligned with the center of curvature of the cornea and is also orthogonal to the cornea surface as has been taught in prior art. Two or more additional position tracking sensors are placed in proximity to the imaging ultrasound transducer in its home position but not on the moveable scan head itself, instead fixed with respect to the positioning mechanism. The minimum number of position tracking sensors will be related to how many axes of motion that expected from the eye during the scan. The alignment of these position tracking sensors is such that they measure the distance to the cornea in close proximity to where the imaging ultrasound transducer also derives its image of the cornea, pupil or posterior surface of the iris in its home position. Prior to any arc scanner movement, a set of distance measurements are taken from the position tracking sensors at the ultrasound imaging transducer is in its home position and in several others positions about the home position effected by known movement of the positioner. This sequence of movements is used to calibrate the distance to the fiduciary eye component. This sequence of preliminary measurements is defined as the tracking calibration sequence.

Similarly the position sensors also measure change in amplitude of reflected signal as another means to track eye movement as any movement of the eye will reflect the position tracking sensor beam (whether ultrasound or optical) in a different direction away from the original reflection causing a change in amplitude of the reflected signal.

Once the tracking calibration sequence is complete, the scanning process can begin. During the scanning process, the fixed position tracking sensors can be monitored at intermediate times during the scan to provide continuous tracking of eye movement in all dimensions and as such correct for any eye movement during the scan.

Figure 9:
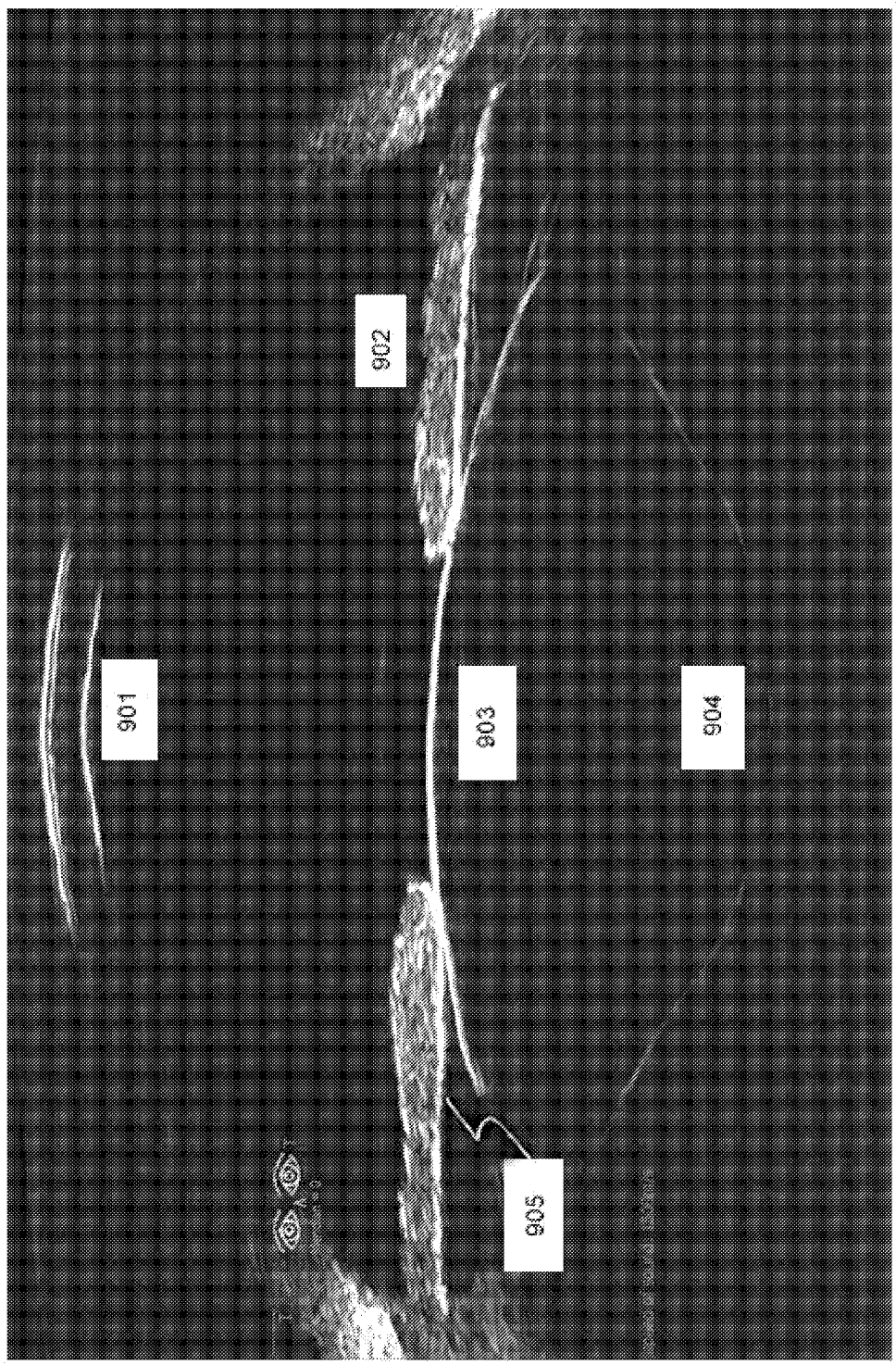
FIG. 9 shows an ultrasound image of the anterior segment of an eye.

As discussed in FIG. 9, the posterior surface of the iris typically appears as a bright line and this can be used to track unintended eye motions by tracking the motion of this feature with a calibrated lower frequency ultrasound transducers (center frequency of the tracking transducer is in the range of about 5 MHz to about 20 MHz). Using the posterior surface of the iris as a fiducial guide is not possible with optical tracking systems.

It is also recognized that this disclosure could be used for ultrasound image scanning of any anatomical feature where there is a point in that anatomical feature that can be referenced and where tracking and compensation of the movement of that anatomical feature during the scan can be carried out.

The Eye

FIG. 1 is a schematic of the main elements of a human eye. The cornea, which is optically transparent, is located at the front of the eye and is located in the anterior chamber. The anterior and posterior surfaces of a normal cornea and the internal layers, such as Bowman's layer, within a normal cornea are specular surfaces. The iris separates the anterior chamber from the posterior chamber. The back of the lens forms the rear of the posterior chamber. The natural lens sits directly behind the iris. Only the central part of the lens, which is behind the pupil, can be seen optically. The anterior and posterior surfaces of a normal lens are specular surfaces. The cornea, iris and lens comprise the main optical refractive components of the eye. The anterior and posterior chambers comprise the anterior segment of the eye. The main volume or posterior segment of the eye lies behind the lens, with the retina and optical nerve at the rear of the posterior segment of the eye. The composition of the eye's aqueous and vitreous humor are very close to that of water with a density of about 1,000 kg/m$^3$, and this allows the eye to be a very good medium for the transmission of acoustic energy.

The optical axis is the line passing through the centers of curvature of the cornea and lens assuming they are centered as they are in a normal eye. The visual axis is the line joining the fixation point and the fovea.

The suprachoroid lies between the choroid and the sclera (see detail in FIG. 1) and is composed of closely packed layers of long pigmented processes derived from each tissue. The suprachoroidal space is normally narrow (about 30 nm thick) and forms a transitional zone between the choroid and sclera. It contains layers of long pigmented collagenous processes forming a closely packed collagen mesh. The suprachoroidal space is a potential space providing a pathway for uveoscleral outflow and becomes an actual space in choroidal detachment. The hydrostatic pressure in the suprachoroidal space is an important parameter for understanding intraocular fluid dynamics and the mechanism of choroidal detachment. The suprachoroidal hydrostatic pressure is 1 or 2 mm Hg less than the intraocular pressure and that the pressure difference was unaffected by intraocular pressure.

Optical means are suitable for viewing the anterior chamber and for viewing near the entire central axis of the eye. However, optical means cannot be used to view the portions of the posterior chamber lying far off-axis and behind the iris because light does not penetrate the iris. These portions include the suspensory ligaments (also known as zonules), the sulcus and the ciliary body. However, the eye components that cannot be viewed optically, can be viewed with suitably high-frequency acoustic energy because high-frequency acoustic energy can readily penetrate the iris. As is well-known, acoustic frequencies in the ultrasonic range of about 5 MHz to about 100 MHz can be used to provide very high resolution images of, for example, the cornea and the lens. The basics of ultrasonic scanning for the eye are described in "Ultrasonography of the Eye and Orbit", Second Edition, Coleman et al, published by Lippincott Williams & Wilkins, 2006. Also, optical means have difficulty measuring the region between the cornea and iris and cannot image stents that are placed near the suprachoroidal space to help relieve the symptoms of glaucoma.

Some of the typical dimensions of the human eye in millimeters and these dimensions apply at least along or near the optical axis.

Thickness of cornea ~0.5 mm
Radius of curvature anterior cornea surface ~7.7 mm
Radius of curvature posterior cornea surface ~6.8 mm
Distance from the front of the cornea to the front of the lens ~3.3 mm
Thickness of lens ~3.5 mm
Radius of curvature anterior lens surface ~11 mm
Radius of curvature posterior lens surface ~-6.0 mm
Equatorial diameter of lens ~8.5 mm to 10 mm
Distance from the rear of the lens to the front of the retina ~16 mm
Typical values for the thicknesses and radii of curvature for the refractive components of the eye are:
Thickness of cornea ~0.5 mm
Radius of curvature anterior cornea surface ~7.7 mm
Radius of curvature posterior cornea surface ~6.8 mm
Thickness of lens ~3.5 mm
Radius of curvature anterior lens surface ~11 mm
Radius of curvature posterior lens surface ~-6.0 mm
The accepted acoustic velocities for some eye component, at 37 C, are:
cornea ~1639 m/s
aqueous humor ~1532 m/s
lens ~1641 m/s
cataractous lens ~1,629 m/s These values are from Table 1.1 of "Ultrasonography of the Eye and Orbit", Second Edition, Coleman et al, published by Lippincott Williams & Wilkins, 2006.

For comparison, the acoustic velocity (also known as the speed of sound) in water at 37° C. is ~1,520 m/s.

A focused ultrasonic transducer has an aperture which is slightly concave with radius of curvature that focuses the acoustic pulses at a desired location. For the example of a transducer with a diameter of 5 mm, a focal length of 15 mm, a center frequency of about 38 MHz, the depth of focus is about 1,560 microns.

As can be appreciated, a transducer with a concave aperture is preferred. In scanning an eye feature of interest, it is typically preferred to place the focal plane of the transducer as close to the feature of interest as possible. Obtaining a strong, sharp image of an eye feature of interest involves fulfilling at least 2 conditions: (1) the focal plane must be located near the feature of interest and (2) the transducer pulse must engage the surface of interest substantially normal to the surface. This latter condition can be fulfilled if the pulse wave train passes through both the center of curvature of the transducer arcuate track guide and the center of curvature of the eye component surface.

Arc scanning machines have demonstrated that they can repeatedly produce an image of eye features as small as about 5 microns in the depth direction (z-direction) and about 50 microns in either lateral direction (x- and y directions). For example, scans of a cornea can image the epithelial layer, Bowman's layer and LASIK flap scars, all in a cornea that is about 500 microns thick. Thus it is important to be able to account for any unintended motions of the patient's head or eye during a scan, especially if multiple scans are made and later spliced together to form a composite image.

Ultrasound Eye Scanning Apparatus

Figure 2:
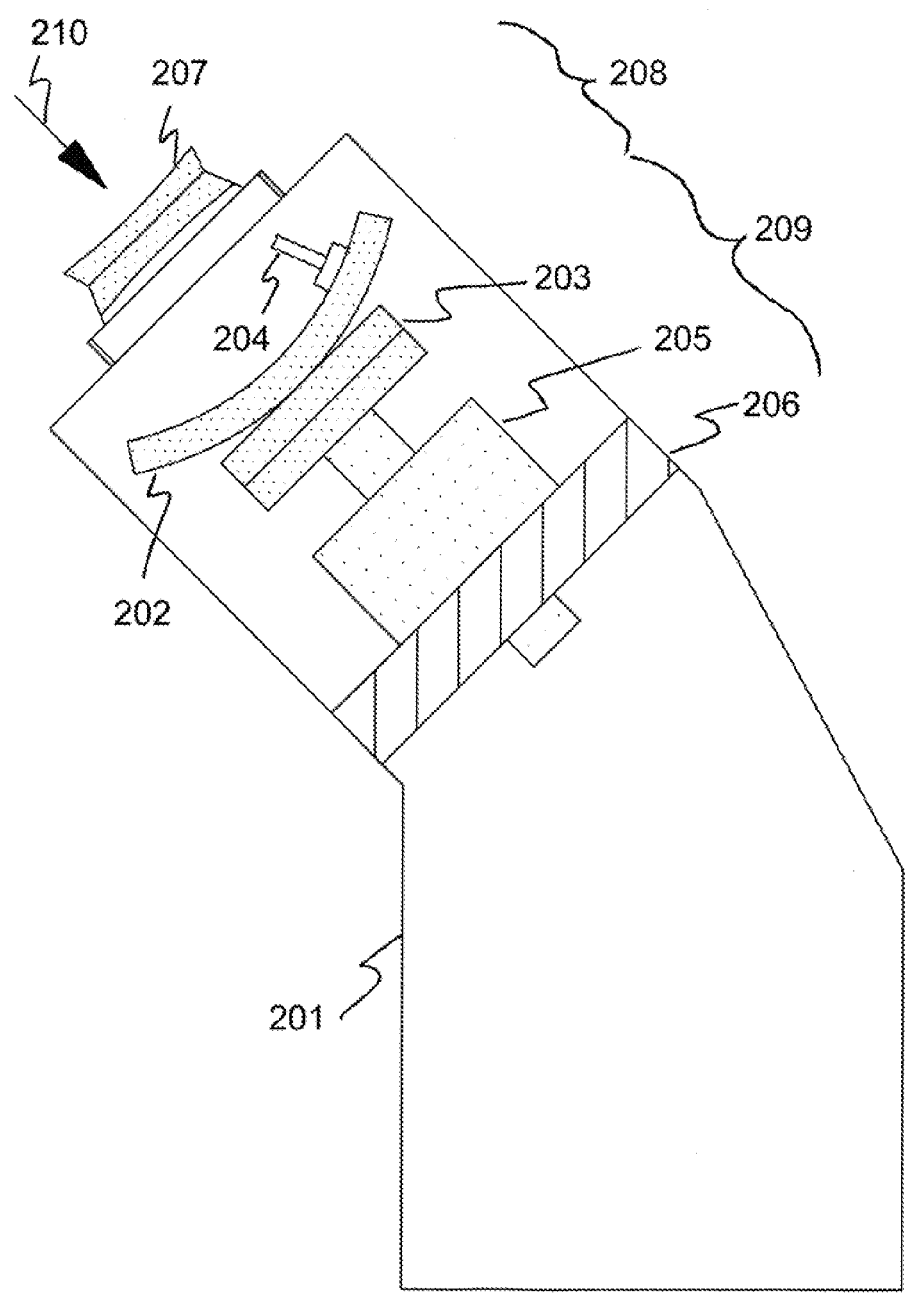
FIG. 2 is a schematic of the principal elements of a prior art ultrasound eye scanning device.

FIG. 2 is a schematic of the principal elements of a prior art ultrasound eye scanning device such as described in U.S. patent application Ser. No. 12/638,661. The scanning apparatus 201 of this example is comprised of a scan head assembly 208 (shown here as an arcuate guide 202 with scanning transducer 204 on a transducer carriage which moves back and forth along the arcuate guide track, and a linear guide track 203 which moves the arcuate guide track back and forth as described in FIG. 4), a positioning mechanism 209 comprised of an x-y-z and beta mechanisms 205 as described in FIG. 3 mounted on a base 206 which is rigidly attached to scanning apparatus 201, and a disposable eyepiece 207. The scanning machine 201 is typically connected to a computer (not shown) which includes a processor module, a memory module, and a video monitor. The patient is seated at the machine 201 with their eye engaged with disposable eyepiece 207. The patient is typically looking downward during a scan sequence. The patient is fixed with respect to the scanning machine 201 by a headrest system such as shown in FIG. 5 and by the eyepiece 207. The operator using, for example, a mouse and/or a keyboard and video screen inputs information into the computer selecting the type of scan and scan configurations as well as the desired type of output analyses. The operator, for example, again using a mouse and/or a keyboard, a video camera located in the scanning machine and video screen, then centers a reference marker such as, for example, a set of cross hairs displayed on a video screen on the desired component of the patient's eye which is also displayed on video screen. This is done by setting one of the cross hairs as the prime meridian for scanning. These steps are carried out using the positioning mechanism which can move the scan head in the x, x, z and beta space (three translational motions plus rotation about the z-axis). Once this is accomplished, the operator instructs computer using either a mouse and/or a keyboard to proceed with the scanning sequence. Now the computer processor takes over the procedure and issues instructions to the scan head 208 and the transducer 204 and receives positional and imaging data. The computer processor proceeds with a sequence of operations such as, for example: (1) with the transducer carriage substantially centered on the arcuate guide track, rough focusing of transducer 204 on a selected eye component; (2) accurately centering of the arcuate guide track with respect to the selected eye component; (3) accurately focusing transducer 204 on the selected feature of the selected eye component; (4) rotating the scan head through a substantial angle (including orthogonal) and repeating steps (1) through (3) on a second meridian; (5) rotating the scan head back to the prime meridian; (6) initiating a set of A-scans along each of the of selected scan meridians, storing this information in the memory module; (7) utilizing the processor, converting the A-scans for each meridian into a set of B-scans and then processing the B-scans to form an image associated with each meridian; (8) performing the selected analyses on the A-scans, B-scans and images associated with each or all of the meridians scanned; and (9) outputting the data in a preselected format to an output device such as a printer. As can be appreciated, the patient's head must remain fixed with respect to the scanning machine 201 during the above operations when scanning is being carried out, which in a modern ultrasound scanning machine, can take several tens of seconds.

An eyepiece serves to complete a continuous acoustic path for ultrasonic scanning, that path extending in water from the transducer to the surface of the patient's eye. The eyepiece 207 also separates the water in which the patient's eye is immersed from the water in the chamber in which the transducer guide track assemblies are contained. The patient sits at the machine and looks down through the eyepiece 207 as shown by arrow 210. Finally, the eyepiece provides an additional steady rest for the patient and helps the patient to remain steady during a scan procedure.

Mechanisms for General Ultrasound Scanning

Figure 3:
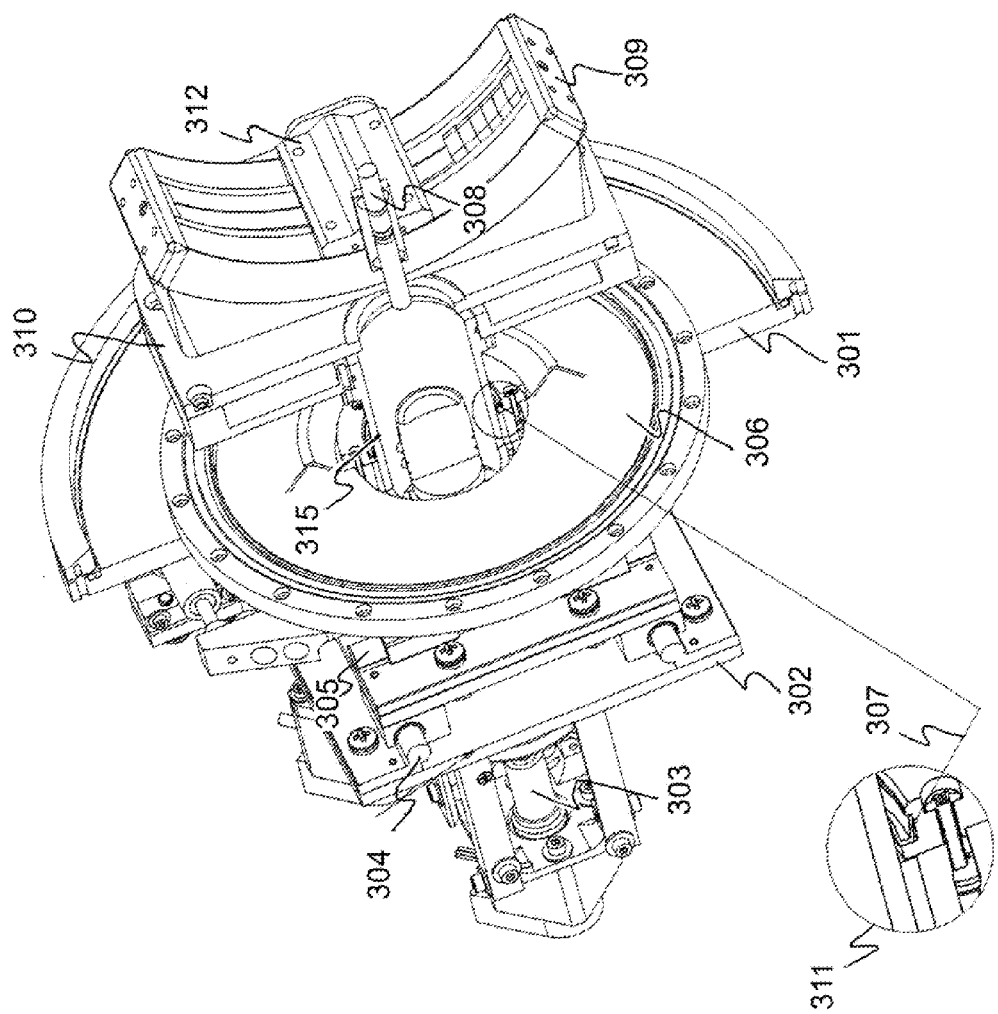
FIG. 3 illustrates a prior art arc scanning head positioning mechanism.

FIG. 3 illustrates a compact arc scan head positioning mechanism which has been disclosed previously in U.S. patent application Ser. No. 12/347,674. FIG. 3 shows a scan head assembly comprised of scan head mount structure 310 and arcuate guide track 309 with ultrasonic transducer 308 mounted on transducer carriage 312. Transducer carriage 312 may be moved back and forth along arcuate guide track 309 to perform an arc scan. The scan head assembly is attached to a main positioner arm 315 (shown in a sectional view). The scan head mount structure 310, arcuate track 309, transducer carriage 312 and scanning transducer 308 are operative under water and are sealed from the rear portion of the positioning mechanism by a translational seal 306 and a rotational seal 307. The translational seal 306 is typically formed by a large rubber membrane that can flex with the small x and y motions required by the scanning head positioner, although alternate sealing mechanisms may be employed. The z-axis seal and rotational seal 307 seal against the main positioner arm 315 which can both rotate and move in and out in the z-direction. Translational seal 306 is attached to stationary plate 301 which, in turn, is affixed to the main arc scanner water tank (not shown) which, in turn, is fixed with respect to the patient being scanned. The z-axis and rotational seal 307, which is shown in close-up view 311, is typically formed by a circumferential groove type sealing mechanism with the groove facing into the water, although alternate sealing mechanisms may be employed. Available seals allow both rotation and axial translation of the center tube while maintaining a water tight seal. Plate 302 forms a platform for the x- and y-positioning mechanisms. Plate 302 is fixed relative to stationary plate 301. The scanning head assembly can be moved back and forth axially (the z-direction) by axial piston 303 or another suitable mechanism. The scanning head assembly can be rotated (the beta-direction) about the z-axis by a rotary stepping motor (not shown) or another suitable device. The scanning head assembly can be moved up and down (the y-direction) by piston 305 or another suitable mechanism. The scanning head assembly can be moved from side to side (the x-direction) by piston 304 or another suitable mechanism. The components to the left or rear of stationary plate 301 remain in ambient air while the components to the right or front of stationary plate 301 are in immersed in water when the arc scanner is operational.

Typically, the scan head assembly is moved in the x-, y-, z- and beta directions to position the scan head assembly with respect to an eye component of interest. Although these motions are typically made rapidly under computer control, scans of the eye are typically not made during positioning. Once the scan head assembly is positioned with respect to the eye component of interest, scans are made by the transducer carriage 312 moving back and forth along the arcuate guide track 309. As described in U.S. patent application Ser. No. 12/347,674, the transducer carriage 312 moves along arcuate guide track 309 on a fluid bearing for smooth operation.

As described above, the scanning head can be moved back and forth axially (the z-direction); rotated (the beta-direction) about the z-axis; moved up and down (the y-direction); and moved from side to side (the x-direction). It is therefore possible to move the entire scan head in more complex motions by coordinating these movements to obtain scans that cannot be obtained by a simple arc scan. However, the mechanisms of the apparatus of FIG. 3, while suitable for rapid positioning movements, are not well-suited for rapid scanning motions necessary, for example, to obtain multiple images of an eye accommodating in real time. A more advanced device is illustrated in FIG. 4.

Figure 4:
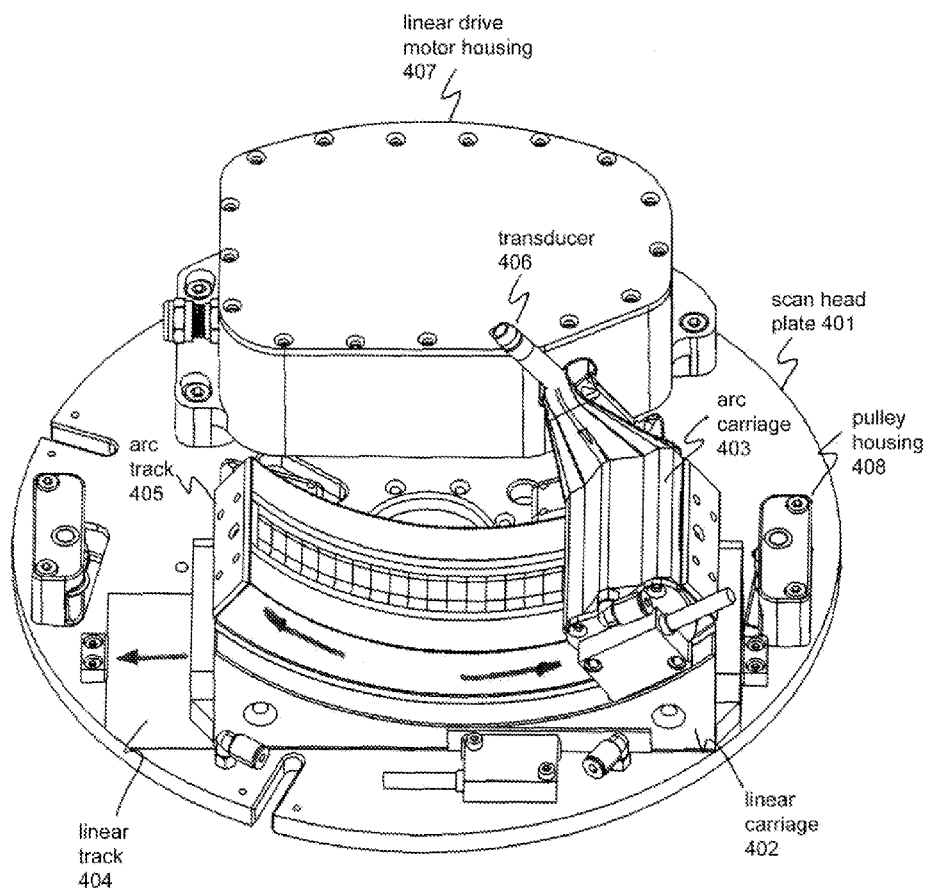
FIG. 4 illustrates a prior art scan head positioning mechanism and scan head capable of arcuate motion.
Figure 5:
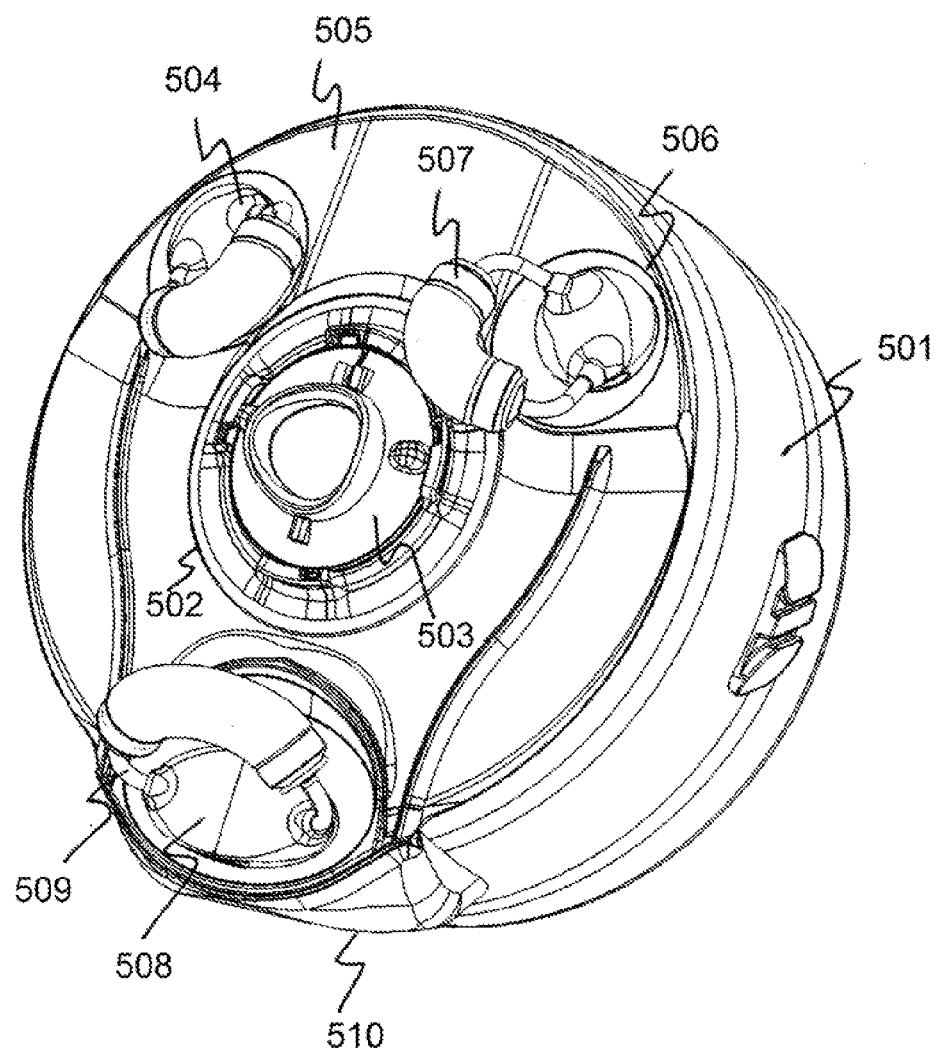
FIG. 5 is a schematic representation of a prior art a headrest for an eye scanning apparatus.

FIG. 4 illustrates a prior art scan head capable of linear motion, arcuate motion and combined linear and arcuate motion. This scan head was disclosed previously in U.S. patent application Ser. No. 12/638,661. The scan head plate 401 replaces scan head mount structure 310 of FIG. 3. Scan head plate 401 serves as the platform for a computer controlled linear carriage 402 and arcuate carriage 403. Linear carriage 402 moves back and forth along linear guide track 404. Arcuate carriage 403 moves back and forth along arcuate guide track 405. In this view, arc carriage 403 is at the rightmost limit of its travel along arcuate guide track 405 and linear carriage 402 is also at the rightmost limit of its travel on linear guide track 404. As can be appreciated, the motions of arc carriage 403 and linear carriage 402 can be controlled independently. For example, arc carriage 403 can move along arcuate guide track 405 or be parked anywhere along arcuate guide track 405 while linear carriage 402 moves along linear guide track 404. As another example, linear carriage 402 can be stationary while arc carriage 403 moves back and forth along arcuate guide track 405 to execute a pure arc scan. When arc carriage 403 is stationary and linear carriage 402 is moved, this is referred to as a linear scan. When both arc carriage 403 and linear carriage 402 are moved, this is referred to as combined scan. In this configuration, arc carriage 403 is moved along arcuate guide track 405 by an induction motor as described in U.S. patent application Ser. No. 12/347,674. Arc carriage 403 moves along arcuate guide track 405 on a fluid bearing which is also described in U.S. patent application Ser. No. 12/347,674. Ultrasound scanning transducer 406 is mounted on arc carriage 403 and the axis of transducer 406 is aligned along the radius of curvature of arcuate guide track 405. Linear carriage 402 is moved along linear guide track 404 by a drive motor (not shown) housed in linear drive motor housing 407. This drive motor moves linear carriage 402 by a belt and pulley system (not shown except for typical pulley housing 408). Linear carriage 402 moves along linear guide track 404 on a fluid bearing similar to that used between arc carriage 403 and arcuate track 405. In operation, the scan head assembly of FIG. 4 is under water and is sealed from the x, y, z, beta positioner (shown in FIG. 3) by a sealing means behind the scan head plate. Thus the entire scanning mechanism is positioned with respect to an eye for scanning by the x, y, z, beta positioner shown in FIG. 3, while the actual acoustic imaging scan motion is implemented by one or both of the linear and arc carriages 402 and 403. The scan head assembly of FIG. 4 allows rapid independent linear and arcuate motion combinations of the transducer such that various scan geometries can be implemented to image not only the cornea, iris and anterior lens surface, but also the posterior lens surface, the sulcus, the ciliary body, the suprachoroidal space and the zonules that attach the lens to the ciliary body.

There is a special combined motion where the linear and arcuate motions are co-ordinated to produce a resultant arcuate motion of larger or smaller radius of curvature than the radius of curvature of the arcuate track. This combined motion is more completely is described in U.S. patent application Ser. No. 12/638,661.

Headrest

FIG. 5 is a schematic representation of an example of a headrest system suitable for the present disclosure. FIG. 5 shows the body of an ultrasonic imaging device 501. The disposable eyepiece 503 is shown attached to an eyepiece retaining ring 502 which is permanently attached to the body of an ultrasound imaging device 501. A headrest system is shown comprising a chin rest 508 and a two temple or forehead rests 504 and 506. The head rest system also includes an independently detachable water collector 510. The water collector 510 may be attached to the scanner body 501 in a variety of ways but preferably by magnetic attachment. Each of the chin rest 508 and two forehead rests 504 and 506 are comprised of a base plate such as 508, two connecting arms such as 509 and a central cushion such as 507. The base plate, connecting arms and central cushion form face rest subassemblies. The base plate of each face rest subassembly can be moved around on a metallic surface 505 which is on the front side (patient side) of the body of the imaging device 501. The underside of each base plate includes a magnet (not shown) which maintains the base plate in contact with the metallic surface such that the face rest subassembly can be readily positioned anywhere on its corresponding metallic surface 505. The underside of each base plate also includes an O-ring (not shown) that forms an air-tight seal around the periphery of the underside of the base plate, thereby forming a seal around most of the underside of the base plate. In the center of the underside of each base plate, there is an orifice that connects a vacuum pathway that goes up through one or both of the arms of the face rest subassembly to the interior of the cushion of the face rest subassembly. When a light vacuum is applied, the face rest subassembly is locked onto the metallic surface and the cushion becomes rigid. The cushions may be constructed by filling a flexible, gas-impermeable containing bag or capsule with a granular material.

The light vacuum is achieved by a small vacuum pump (not shown) which is connected via vacuum tubing to a small surge plenum. There are three separate vacuum lines from the surge plenum, one to each of the face rest subassemblies. Each of the three separate vacuum lines terminates at an orifice in the center of each of the three metallic surfaces on the face of the body of the imaging device 501. Each of the three separate vacuum lines has a check valve that is closed when there is no pressure differential across the valve. The check valve opens when a vacuum is being pulled but will close when the pressure differential across the valve is reduced to about zero. Each face rest subassembly has a small button that, when depressed, releases the vacuum under the base plate so that face rest subassembly can be moved while the other two face rest subassemblies remain under vacuum and hence remain fixed. This temporary vacuum release is made possible by the check valves in the vacuum lines. As can be appreciated, when there is no vacuum, any or all of the face rest subassemblies can be removed by pulling up with enough force to overcome the magnetic attachment. When a face rest subassembly is removed, its vacuum connection is manually or, preferably, automatically closed off, thereby allowing the remaining face rest subassemblies to remain active.

During the adjustment phase, the face rest subassemblies are moved around to best fit the patient's temples and chin. During this time, the cushions are maintained close the ambient atmospheric pressure so that there is little pressure differential between the inside and outside of the cushions. With differential pressures in the range from about −0.01 atmosphere (−0.147 psi) to about +0.03 atmosphere (+0.441 psi), the cushion is easily deformed when the patient places his or her head or chin firmly in contact with it. This causes the cushions of each face rest subassembly to conform to the temples and chin in such a way as to allow small adjustments of the head position to permit alignment with sealing devices or imaging components. For example, in the illustration of the ultrasonic scanner, the patient must make small adjustments to align his or her eye with a scanning reference beam while also maintaining a seal between his or her face and a flexible eyepiece.

When the head is aligned and the patient is comfortable, the vacuum system is pumped to a lower pressure, causing atmospheric pressure to force the face rest subassemblies into rigid contact with their corresponding metallic surfaces and to force the cushions' coverings to press firmly against the contained granular material. This simultaneously locks each face rest subassembly in place and locks the granular material in each cushion into place, maintaining the outer form of the cushion against subsequent movements of the head and holding the head rigidly in the desired position and alignment.

The cushions may be covered with a disposable paper, plastic or other covering to protect the cushions from patient's perspiration etcetera and to protect the patient from other patient's perspiration etcetera.

An advantage of this embodiment is that each face rest subassembly is independently movable and the entire headrest system can be locked tight once the patient is in a comfortable position with respect to the scanner and with their eye properly positioned in the eyepiece. Another advantage of this embodiment is the face rest subassemblies have a relatively low profile and this allows the operator to see around the cushions to determine if the patient is properly positioned and to see any problems that the patient may be having with the seal between their face and the eyepiece. Another advantage of this embodiment is that any one of the face rest subassemblies may be removed if the operator deems this necessary. This headrest system is fully described in U.S. patent application Ser. No. 12/754,444.

Eyepiece

An eyepiece serves to complete a continuous acoustic path for ultrasonic scanning, that path extending from the transducer to the surface of the patient's eye. The eyepiece also separates the water in which the patient's eye is immersed from the water in the chamber in which the positioner and scan head assemblies are contained. Finally, the eyepiece provides a reference frame for the patient and helps the patient to remain steady during a scan.

An eyepiece that satisfies these requirements typically consists of a mounting ring and an eye seal ring. The mounting ring is attached to and is typically a permanent part of the main arc scanner assembly. The mounting ring has several attachment grooves which can accept attaching mechanisms on the eye seal ring. The eye seal ring has a soft rubber or foam contoured face seal which is designed to seal against a typical human face around the eye that is to be scanned.

Figure 6:
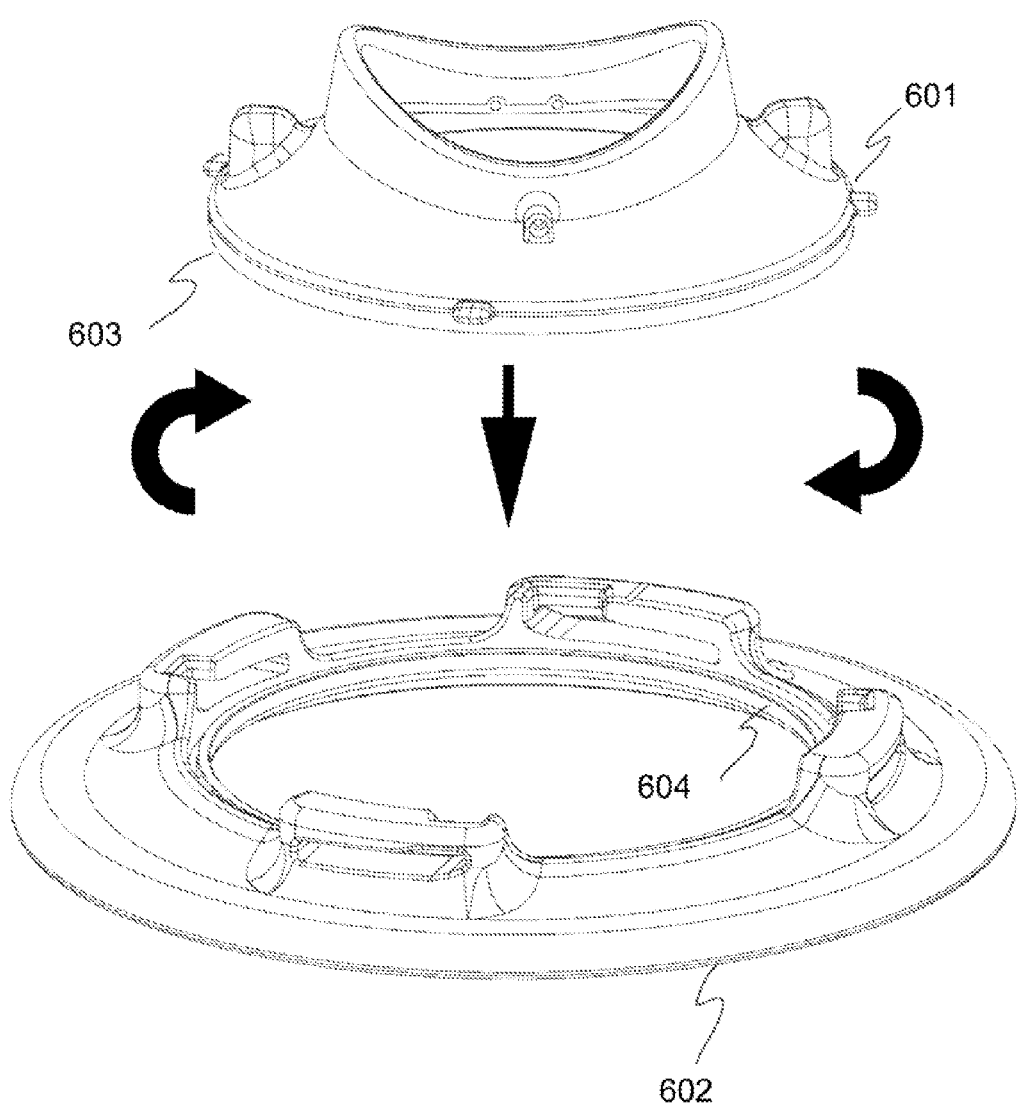
FIG. 6 illustrates a typical embodiment of a prior art eyepiece for an ultrasonic eye scanner.

FIG. 6 illustrates a typical embodiment of an eyepiece for an arc scanner. The eyepiece consists of a mounting ring 602 and an eye seal ring 601. The mounting ring 602 is attached to the main arc scanner assembly and is typically a permanent part of the main arc scanner assembly. As shown here the mounting ring 602 has several attachment grooves which can accept attaching mechanisms on the eye seal ring 601. In this embodiment, the attaching mechanisms are pushed down into the attachment grooves and then rotated into position to form a mechanical connection that seals the eye seal ring against the mounting ring to prevent water leakage. This is also known as a bayonet type connection. There is an additional sealing feature consisting of a groove 603 molded as part of the eye seal ring 601 and a matching tongue 604 molded as part of the mounting ring 602. When the eye seal ring 601 is rotated into position with the mounting ring 602, the tongue and groove form a threaded connection which compresses as the parts are rotated into position. This is similar in sealing action of a plastic bottle with a threaded top. Since both the eye seal ring 601 and the mounting ring 602 are typically made from a plastic, the compliance of the plastic further helps in forming a water tight seal. The eye seal ring 601 has a soft rubber or foam face seal (not shown here) which is designed to seal against a typical human face around the eye that is to be scanned. A sealed hygienic barrier (not shown) is formed as part of the eye seal ring 601 and is typically located where the contoured face seal is connected to the main body of the eye seal ring 601.

As described previously, the eye seal ring typically includes a soft rubber or foam contoured face seal which is designed to seal against a typical human face around the eye that is to be scanned. The contoured face seal may also be made from a foam material impregnated with, for example, mineral oil, to provide a superior sealing action against a typical human face around the eye. An alternative face sealing mechanism can also be provided by a hollow soft rubber or soft plastic ring molded into the removable eye seal ring that can be filled with water after the patient has placed their face against the eyepiece. This eyepiece is more completely described U.S. patent application Ser. No. 12/347,674.

PRESENT DISCLOSURE

Figure 7:
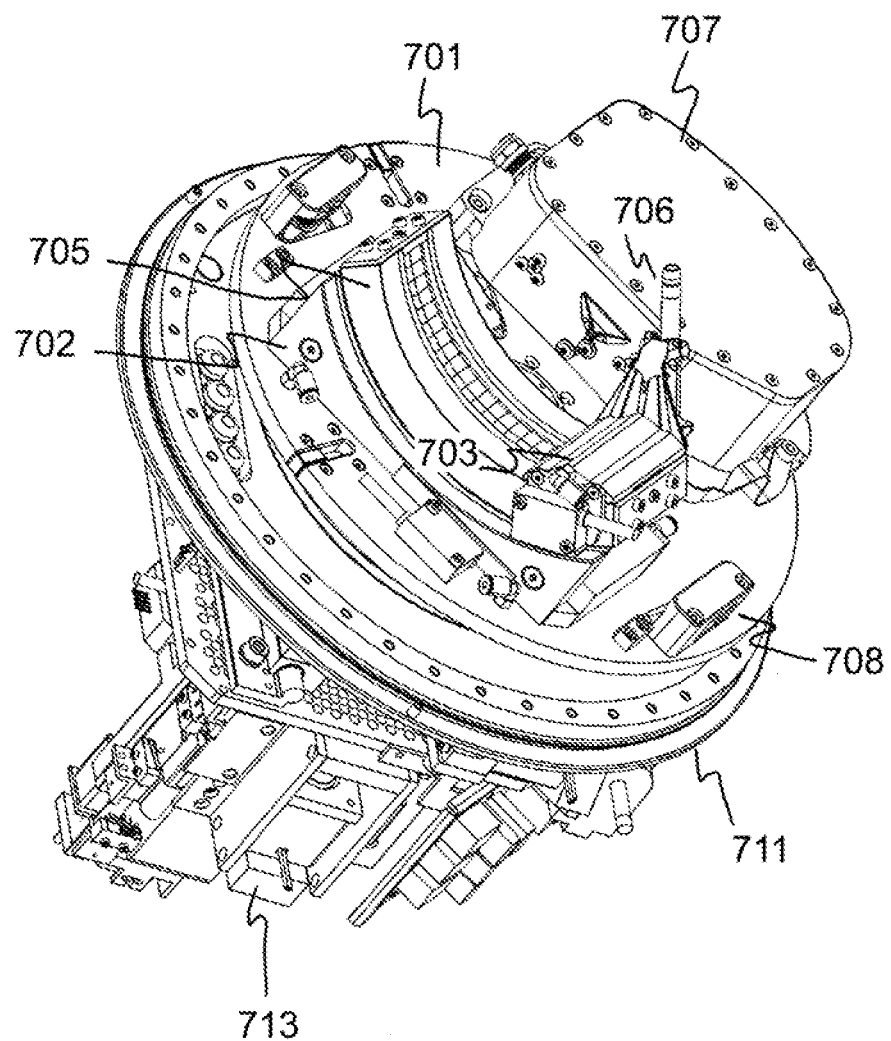
FIG. 7 illustrates a scan head positioning mechanism and scan head capable of combined motion.

FIG. 7 illustrates a scan head capable of combined motion. This figure is similar to that of FIG. 3, except that the arcuate motion scan head has been replaced by a combined motion scan head such as shown in FIG. 4. FIG. 7 shows a combined scan head assembly comprised of a scan head plate 701 which serves as the platform for a computer controlled linear carriage 702 and arcuate carriage 703. Linear carriage 702 moves back and forth along its linear guide track. Arc carriage 703 moves back and forth along arcuate guide track 705. As can be appreciated, the motions of arc carriage 703 and linear carriage 702 can be controlled independently. When arc carriage 703 is stationary and linear carriage 702 is moved, this is referred to as a linear scan. When both arc carriage 703 and linear carriage 702 are moved, this is referred to as combined scan. Ultrasound scanning transducer 706 is mounted on arc carriage 703 and the axis of transducer 706 is aligned along the radius of curvature of arcuate guide track 705. Linear carriage 402 is moved along its linear guide track by a drive motor (not shown) housed in linear drive motor housing 707. This drive motor moves linear carriage 702 by a belt and pulley system (not shown except for typical pulley housing 708). Linear carriage 702 moves along its linear guide track on a fluid bearing similar to that used between arc carriage 703 and arcuate track 705. In operation, the scan head assembly of FIG. 7 is under water and is sealed from the x, y, z, beta positioner 713 shown to the bottom left of scan head plate 701 by a sealing means behind the scan head plate. Thus the entire scanning mechanism is positioned with respect to an eye for scanning by the x, y, z, beta positioner, while the actual acoustic imaging scan motion is implemented by one or both of the linear and arc carriages 702 and 703. The scan head assembly of FIG. 7 allows rapid independent linear and arcuate motion combinations of the transducer such that various scan geometries can be implemented to image not only the cornea, iris and anterior lens surface, but also the posterior lens surface, the sulcus, the ciliary body, the suprachoroidal space and the zonules that attach the lens to the ciliary body.

Typically, the scan head assembly is moved in the x-, y-, z- and beta directions to position the scan head assembly with respect to an eye component of interest as described previously in FIG. 3. Although these motions are typically made rapidly under computer control, scans of the eye are typically not made during positioning. Once the scan head assembly is positioned with respect to the eye component of interest, scans are made by the transducer carriage 703 moving back and forth along the arcuate guide track while the arc carriage 703 is moved back and forth by the linear carriage. As described above, the scanning head can be moved back and forth axially (the z-direction); rotated (the beta-direction) about the z-axis; moved up and down (the y-direction); and moved from side to side (the x-direction). It is therefore possible to move the entire scan head in more complex motions by coordinating these movements to obtain scans that cannot be obtained by a simple arc scan.

The headrest and the eyepiece act to comfortably fix the patient's head and eye relative to the eye scanning apparatus. However, it is possible during scanning that the patient's head or eye may move relative to the eye positioning apparatus. Unintended head motions are generally not large in the z-direction because of the constraints of the headrest and eyepiece. Unintended eye motions are generally rotational movements of the eyeball in its socket and are typically saccades (quick, simultaneous rotations of both eyes in the same direction involving a succession of discontinuous individual rotations of the eye orbit in the eye socket). Either of these type of motions can blur a high resolution cornea scan or cause small misalignments when several scans are overlaid to make a composite image.

Figure 8:
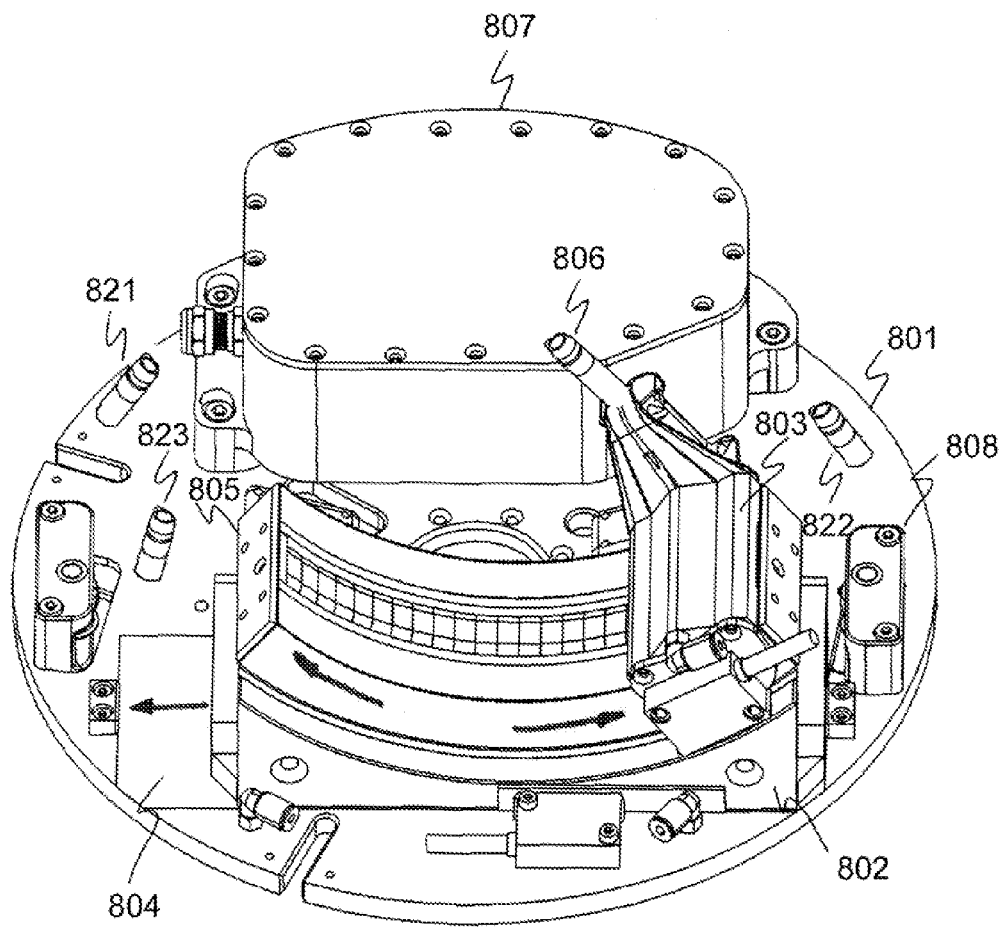
FIG. 8 illustrates a scan head capable of combined motion and where tracking sensors are located on the base of the scan head.

FIG. 8 illustrates a scan head capable of combined motion and where tracking sensors are located on the base of the scan head which is the mounting plate which rigidly connects the scan head to the positioning mechanism. This is the same scan head positioning mechanism and scan head as shown in FIG. 4 and FIG. 7 except that there are 3 tracking sensors, 821, 822 and 823 shown mounted on scan head base plate 801. Scan head base plate 801 serves as the platform for a computer controlled linear carriage 802 and arc carriage 803. Linear carriage 802 moves back and forth along linear guide track 804. Arc carriage 803 moves back and forth along arcuate guide track 805. In this view, arc carriage 803 is at the rightmost limit of its travel along arcuate guide track 805 and linear carriage 802 is also at the rightmost limit of its travel on linear guide track 804. As can be appreciated, the motions of arc carriage 803 and linear carriage 802 can be controlled independently. For example, arc carriage 803 can move along arcuate guide track 805 or be parked anywhere along arcuate guide track 805 while linear carriage 802 moves along linear guide track 804. As another example, linear carriage 802 can be stationary while arc carriage 803 moves back and forth along arcuate guide track 805 to execute a pure arc scan. When arc carriage 803 is stationary and linear carriage 802 is moved, this is referred to as a linear scan. When both arc carriage 803 and linear carriage 802 are moved, this is referred to as combined scan. In this configuration, arc carriage 803 is moved along arcuate guide track 805 by an induction motor as described in U.S. patent application Ser. No. 12/347,674. Arc carriage 803 moves along arcuate guide track 805 on a fluid bearing which is also described in U.S. patent application Ser. No. 12/347,674. Ultrasound scanning transducer 806 is mounted on arc carriage 803 and the axis of transducer 806 is aligned along the radius of curvature of arcuate guide track 805. Linear carriage 802 is moved along linear guide track 804 by a drive motor (not shown) housed in linear drive motor housing 807. This drive motor moves linear carriage 802 by a belt and pulley system (not shown except for typical pulley housing 808). Linear carriage 802 moves along linear guide track 804 on a fluid bearing similar to that used between arc carriage 803 and arcuate track 805. In operation, the scan head assembly of FIG. 8 is under water and is sealed from the x, y, z, beta positioner (shown in FIGS. 3 and 7) by a sealing means behind the scan head base plate. Thus the entire scanning mechanism is positioned with respect to an eye for scanning by the x, y, z, beta positioner shown in FIG. 7, while the actual acoustic imaging scan motion is implemented by one or both of the linear and arc carriages 802 and 803. The scan head assembly allows rapid independent linear and arcuate motion combinations of the transducer such that various scan geometries can be implemented to image not only the cornea, iris and anterior lens surface, but also the posterior lens surface, the ciliary body, the suprachoroid space and the zonules that attach the lens to the ciliary body.

The 3 tracking sensors, 821, 822 and 823 mounted on scan head plate are fixed with respect to the scan head positioning mechanism. Once the patient is securely positioned in the eyepiece with the head rest set, the scanning ultrasound transducer is set at its home position and the scan head positioning mechanism is moved in x, y, z and beta until the transducer is centrated on the eye component of interest. This centration process may be done automatically using a centration algorithm or it may be done manually or it may be done manually with a final centration using a centration algorithm. These procedures are discussed in U.S. patent application Ser. Nos. 12/418,392 and 12/638,661.

Now a scan set is initiated. A scan set is a pre-programmed sequence of scan head motions. For example, a cornea scan set might comprise a number of arc scans (the transducer only moves back and forth on the arcuate track) and the scan head is rotated thru a series of angles between each arc scan so that the cornea is imaged at any number of meridians. An anterior segment scan might consist of an arc scan and two linear scans all at a fixed meridian (no beta rotation). The transducer may be parked at an angle with respect to the center of the arc for one linear scan and then at the negative of the angle with respect to the center of the arc for the second linear scan. As can be appreciated any number of arc scans, linear scans or combination arc/linear scans can be made. Each individual scan may be completed in less than a second and a series of scans may be completed in several seconds.

Patient eye motion has been observed in sub-second scans. The longer the time it takes to do a selected scan set, the more likely there will be some patient eye movement. The problem of patient eye movement cannot be solved by moving the transducer faster since eventually the motion of the transducer will cause disturbances in the water which will induce vibrations in the scanning machine itself. This problem typically occurs before cavitation is triggered.

Therefore, it is an objective of the present disclosure to disclose means of tracking any unwanted patient eye movement during a scanning operation and either 1) cause the positioning head to move in response to compensate for patient eye motion; 2) correct the image for this motion in real-time or near real-time or later during post-processing after the scan is complete; 3) warn the patient and/or the operator of patient eye movement above one or more selectable thresholds; and/or 4) instruct the scanning machine to automatically abort the scan if the detected movement is above a predetermined threshold and have the instrument automatically redo the entire scan sequence (e.g. in the case of a multi-meridian scan) or redo only that individual scan on which the motion was detected and then continue scanning.

Actions 1) and 2) can be accomplished if high precision stepper motors are used in the scan head positioning apparatus. In current designs, the stepper motors used in the scan head positioning apparatus and the software has not been developed to allow the scan head positioning apparatus to rapidly adjust to follow and compensate in real time for unintended eye movements. However, tracking transducers can be readily used to measure the patient eye motion relative to the positioning mechanism and correct the image for this motion during image processing.

The tracking sensors, 821, 822 and 823 mounted on scan head plate 801 in FIG. 8 can be ultrasound or optical sensors. These would be positioned to focus on an eye structure at or near the center of the eye. A system of 3 tracking sensors would allow tracking of eye motion in the x-y plane as well as motion along in the z-axis. The system would also be capable, in some circumstances, of sensing any movement of the eye in its socket.

For example, tracking transducers 821, 822 and 823 could be transducers in the frequency range of about 5 to about 20 MHz, focused in the region around the center of the front of the cornea. The tracking transducers would be positioned so that they reflect their acoustic pulses substantially perpendicularly from the front of the cornea. The scanning transducer is typically in the 50 to 80 MHz range and the tracking transducers, since they are most likely further away from the eye, would have to be a low enough frequency to minimize signal attenuation through a longer acoustic path but high enough frequency to provide adequate resolution for tracking small eye movements.

If the eye movement were purely along the z-axis, all the tracking transducers would have a calculable change in time of arrival signal that is a function of their position, orientation and nominal distance from the front surface of the cornea. If the eye movement were purely in the x-y plane, the time of arrival would increase for at least one of the tracking transducers and decrease for at least one of the other transducers.

In other applications, a portion of an ellipse can be fitted to the front surface of the image of the cornea during post-processing. This can be used to help determine rotational movement of the eye such as would occur if the eye rotates slightly in its socket when there is no movement of the head relative to the scanning apparatus.

The signal amplitudes of the tracking transducers can also be useful for determining complex eye movements during scanning. For example, if a signal amplitude decreases while the time-of-arrival remains substantially unchanged, this would indicate a change in the angle of incidence away from perpendicular reflection and thus would be indicative of eye rotation within the eye socket or a slight tilting of the patient's head.

As can be appreciated, 2, 3 or more tracking transducers can be used to determine unintended eye movements using both time-of-arrival and amplitude variation information to develop image post-processing algorithms for compensating for the unintended eye movements. With the use of precision stepper motors for the scan head positioning mechanisms and with state estimation algorithms, it may be possible in the future to allow the scan head positioning mechanisms to compensate for unintended eye movements in real time.

As can be further appreciated, optical sensors can be used for tracking unintended eye movements or combinations of optical and acoustic sensors can be used for tracking unintended eye movements. Other types and/or combinations of sensors for tracking of eye movements as known to those skilled in the art may be used.

In one embodiment, the determination of eye position is resolved through the use of state estimation or signal processing algorithms. That is, algorithms that calculate the "state" of a particular parameter of a system or component by processing the available information. For example, the x-y-z position or state of an object might be calculated by processing a measurement of the x-y-z position by one or more sensors and accounting for the inherent error of the one or more sensors. Models of the sensor error, and any kinematics inherent in the object, are blended to determine, or "estimate," the positional "state" of the object. Here, for example, in an embodiment in which three ultrasonic sensors are each measuring the x-y-z position of the eye and each sensor has a known accuracy profile (or one that can be modeled), a state estimation algorithm would blend the three measurements, accounting for sensor errors, to determine and provide one x-y-z eye position measurement. The particular state estimation algorithm or technique used may be any known to those skilled in the art, to include stochastic signal processing and Kalman filtering.

The head and eye socket of the patient is positioned firmly with respect to the positioning mechanism of the scanning machine by the combination of the heat rests and the eyepiece and these two systems substantially prevent lateral motion of the patients head. There can be some motion of the patients head in the z-direction due to compliance of the soft seal of the eyepiece. This type of motion would give a constant z-displacement of the tracking transducers. The predominant unintended motion during scanning is expected to be rotation of the eyeball in the eye socket and these would be due to saccades which are quick, simultaneous rotations of both eyes in the same direction involving a succession of discontinuous individual rotations of the eye orbit in the eye socket.

The tracking transducers of the present disclosure are therefore placed so as to best detect unintended rotational movements of the eye during scanning. Therefore it is important to use a feature of the eye that is sensitive to rotational movement and is easily imaged by a scanning transducer of the ultrasonic scanner. One such feature is the posterior or rear surface of the iris which typically appears as a bright line in both linear and arcuate scans.

FIG. 9 shows a typical ultrasound image of the anterior segment of an eye which includes a cornea 901, an iris 902, an anterior surface of a lens 903 and much of a posterior surface of the lens 904. The anterior and posterior surfaces of the cornea and lens are specular surfaces which reflect most of the impinging acoustic pulses according to known optical laws of specular reflection. The iris, on the other hand, comprises non-specular tissue and reflects incoming acoustic pulses over a wide range of angles centered approximately around the incident angle. As can be seen, the rear surface of the iris 905 typically appears as a bright line and this posterior pigment layer of the iris can be used to track unintended eye motions by tracking the motion of this feature with a calibrated lower frequency ultrasound transducers (center frequency of the tracking transducer is in the range of about 5 MHz to about 20 MHz).

This figure also illustrates other features of the eye that may be used as fiducial markers for tracking unintended eye motions. These include but are not limited to the anterior or posterior surface of the cornea, the posterior apex or pole of the lens (which can be imaged even with a pure arc scan), the anterior or posterior surface of the lens, the inside edge of an iris that defines the pupil and a posterior surface of an iris (such as the posterior pigment layer of the iris as described above).

Figure 10:
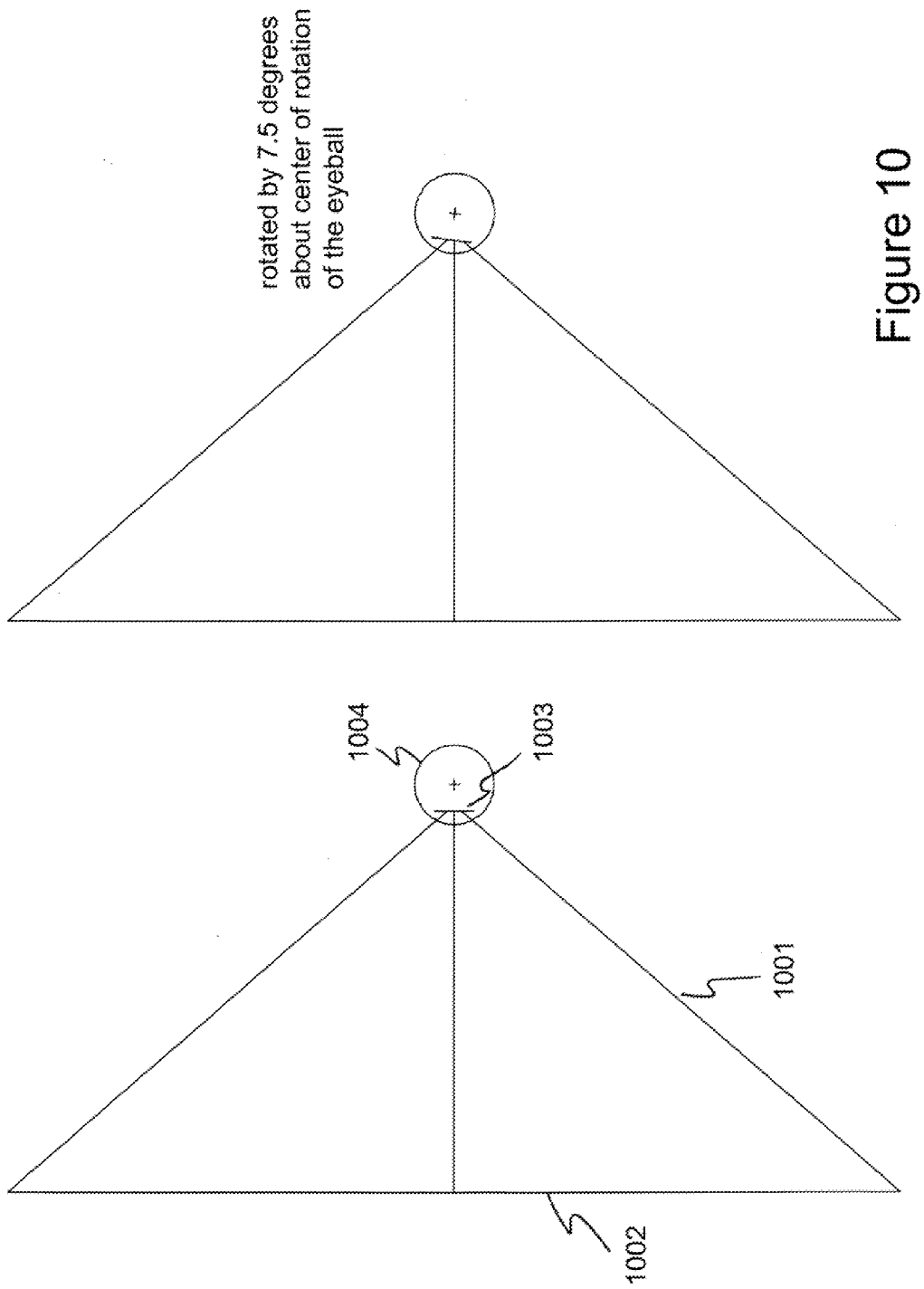
FIG. 10 illustrates an overview of an ultrasound system for detecting motion of the back of an iris.

FIG. 10 illustrates an overview of an ultrasound system for detecting motion of the posterior pigment layer of an iris based on the tracking transducers shown in FIG. 8. The diameter of the circle 1002 on which the tracking transducers are positioned on the base plate that attaches the scan head to the positioning mechanism is about 250 mm. The distance from transducer element to the disc 1003 representing the posterior surface of the iris is about 160 mm as shown by ray 1001. The eyeball 1004 is represented as a 22 mm diameter sphere. The posterior surface of the iris is represented by disc with an outside diameter of about 11 mm and an inside diameter (the diameter of the pupil) of about 3 mm.

If the eye rotates about 7.5 degrees about its center of rotation, then the length of the ray from the upper tracking transducer to the posterior surface of the iris increases by about 0.58 mm (580 microns) and the length of the ray from the lower tracking transducer to the posterior surface of the iris decreases by about 0.26 mm (260 microns).

Taking the speed of sound in water as about 1,500 m/s, then the time difference, $\Delta t$, of the ray from the upper tracking transducer to the posterior surface of the iris increases by about 0.39 μsec and the $\Delta t$ of the ray from the lower tracking transducer to the posterior surface of the iris decreases by about 0.17 μsec. These time variations are easily resolved by the 200 MHz A/D system on the ultrasonic scanner using approximately 10 MHz tracking transducer pulses.

The cornea is about 0.5 mm thick and a sound pulse crosses the cornea in about 0.33 μsec. The system used for ultrasound scanning can resolve features of about 20 microns which would have an acoustic transit time of about 0.013 μsec. The 10 MHz tracking transducers could therefore resolve an angular rotation of about 1 degree.

Figure 11:
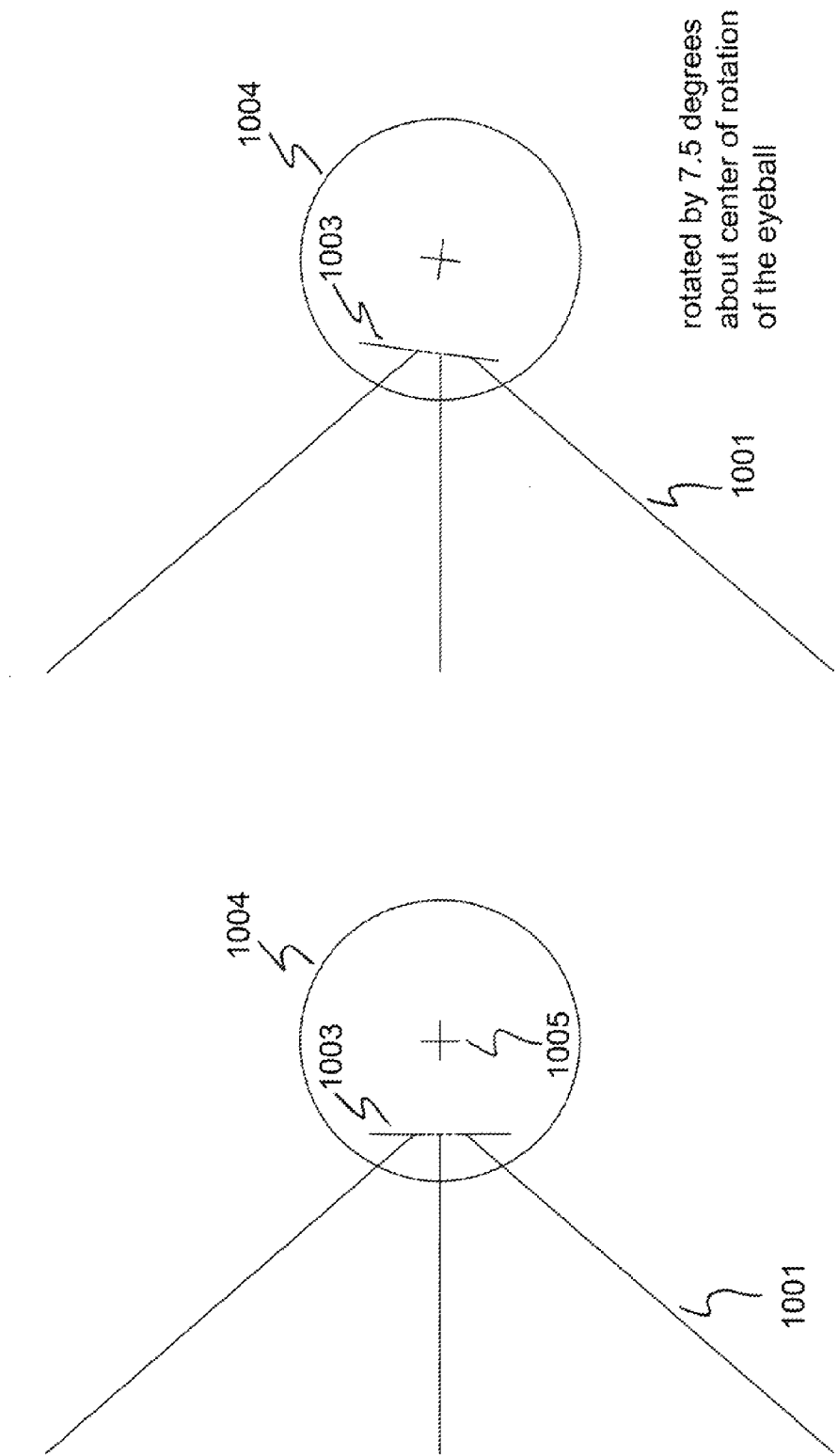
FIG. 11 illustrates a close-up view of an ultrasound system for detecting motion of the back of an iris.

FIG. 11 illustrates a close-up view of FIG. 10 for the ultrasound system for detecting motion of the posterior pigment layer on an iris based on the tracking transducers shown in FIG. 8. The eyeball 1004 is represented as a 22 mm diameter sphere with center of rotation 1005. The posterior surface of the iris is represented by disc 1003 with an outside diameter of about 11 mm and an inside diameter (the diameter of the pupil) of about 3 mm.

Figure 12A:
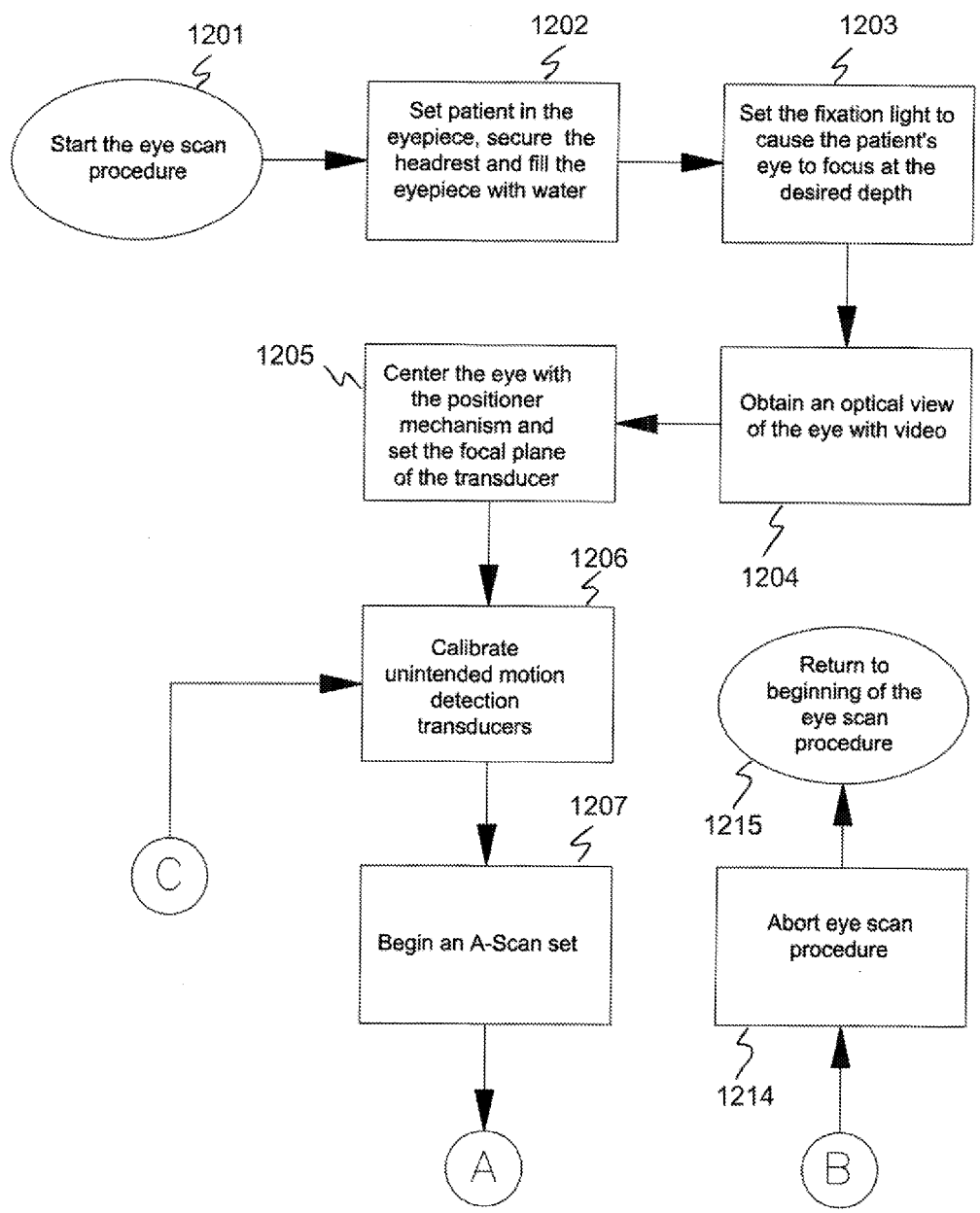
FIGS. 12a and 12b show a flow chart for a simple motion tracking system for selecting or rejecting an ultrasound scan.
Figure 12B:
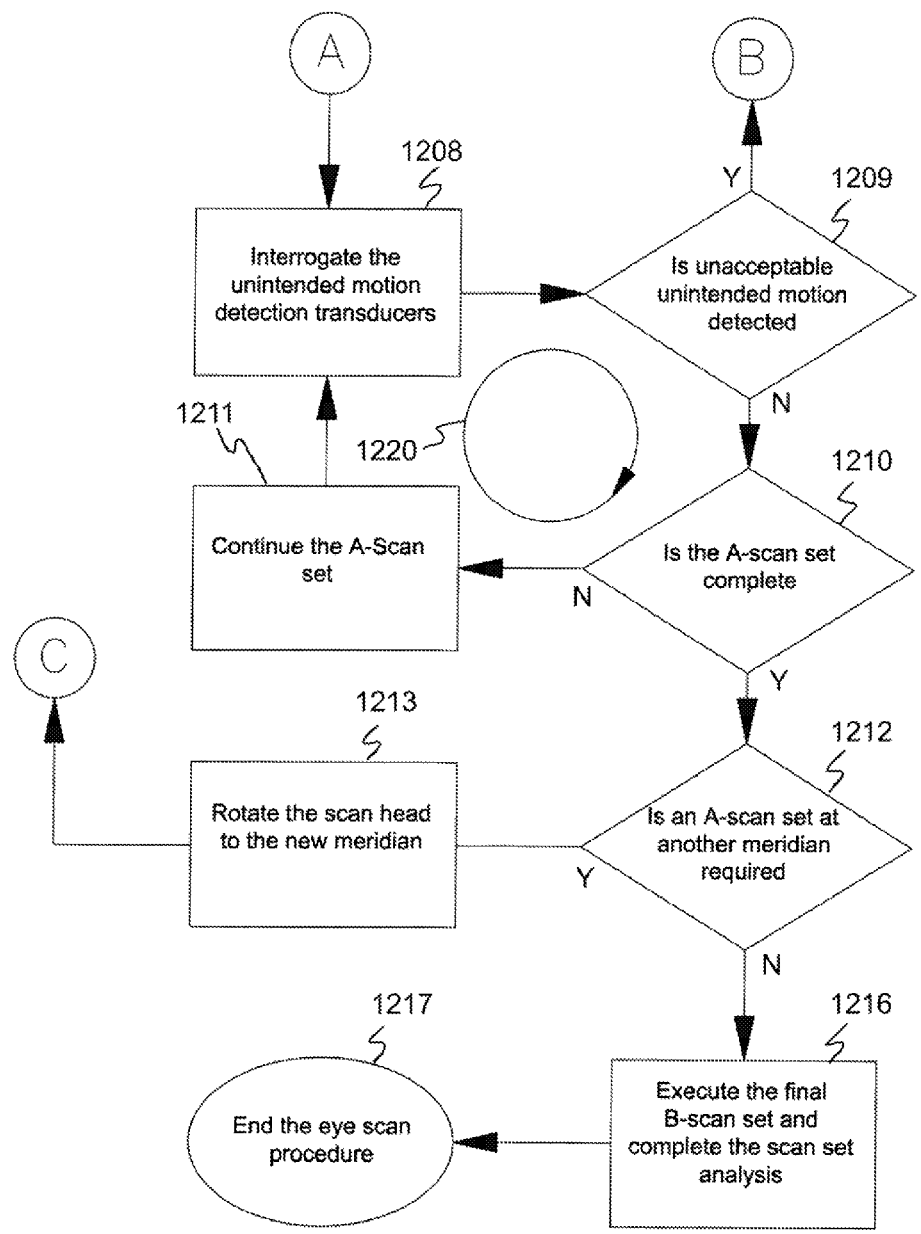

FIGS. 12a and 12b show a flow chart for a possible simple motion tracking system for selecting or rejecting an ultrasound scan. An eye scan procedure as described herein consists of a series of ultrasound scans. These may be several corneal scans at different meridians; several anterior segment scans at different meridians; several full capsule scans at different meridians; or all of these at one session. A scan procedure 1201 begins with the patient sitting, placing their head in a headrest such as shown in FIG. 5 and then placing the eye to be scanned in an eyepiece such as shown in FIG. 6. This firmly fixes the patient's head and eye socket with respect to the scan machine. The eyepiece is then filled with a warm saline solution to complete the water path between the eye and the ultrasound transducers. In the next step 1203, the patient focuses on a fixation target which is typically a low intensity visible light target that is fixed with respect to the positioning mechanism. A video camera, also fixed with respect to the positioning mechanism, in the scanner gives the scanner operator a visual picture of the eye in step 1204 which is used for centration. In step 1205, the scanner operator using a combination of visual observations, optical Purkinje reflections and ultrasound A-scans to center the eye with respect to the ultrasound scanning transducer which itself is centered on the scan head, using the positioning mechanism described in FIG. 3. Also in step 1205, the operator uses the A-scan to set the focal point of the ultrasound transducer at the desired location (approximately along the visual axis in the center of the cornea for corneal scans; approximately along the visual axis half way between the cornea and lens for an anterior segment scan; and approximately along the visual axis in the center of the lens for a lens capsule scan). At this point the operator turns over the operation of the scanner to the computer which has been pre-programmed to carry out a desired scan set. In step 1206, the unintended motion detection transducers are calibrated by sending a series of ultrasound pulses to reflect from a desired eye component (for example, the cornea, the anterior or posterior lens surface or the back of the iris). These calibration pulses are used to determine a series of anchor points or a curve fit to a surface which should remain stationary during the acquisition of the scan set. In step 1207, the set of A-scan acquisitions begins. At selected intervals (for example after every 10 or 20 A-scans, the unintended motion detection transducers are interrogated in step 1208 to determine if their anchor points or fitted surface has moved enough to compromise the scan set. If unacceptable unintended motion is detected in step 1209, then the eye scan procedure is aborted in step 1214 and the computer is returned in step 1215 to the beginning of the eye scan procedure. If unacceptable unintended motion is not detected in step 1209, then if the A-scan set is not complete (step 1210), then the acquisition of the A-scan set is continued in step 1211. As can be seen, the acquisition of A-scans and unintended motion calibration is continued as indicated by logic loop 1220. If the A-scan set is complete (step 1210) then if another A-scan set is required at a different meridian, then the scan head is rotated by the positioner to the new meridian in step 1213 and the program is directed back to step 1206 to begin re-calibration of the unintended motion detection transducers. If another A-scan set is not required at a different meridian, then the scanning is complete and the computer automatically advances in step 1216 to the analysis of the A-scans and the construction of the desired B-scans (that is, the final ultrasound images). Then the eye scan procedure is completed (step 1217). At this point the water in the eye seal is drained and the patient is free to leave or undergo another eye scan procedure on their other eye.

The procedure described in FIG. 12 may be applied when unintended motion is detected but the data is insufficient to correct for the unintended motion. In this case, the procedure or sub-procedure is aborted and restarted from the beginning.

Figure 13A:
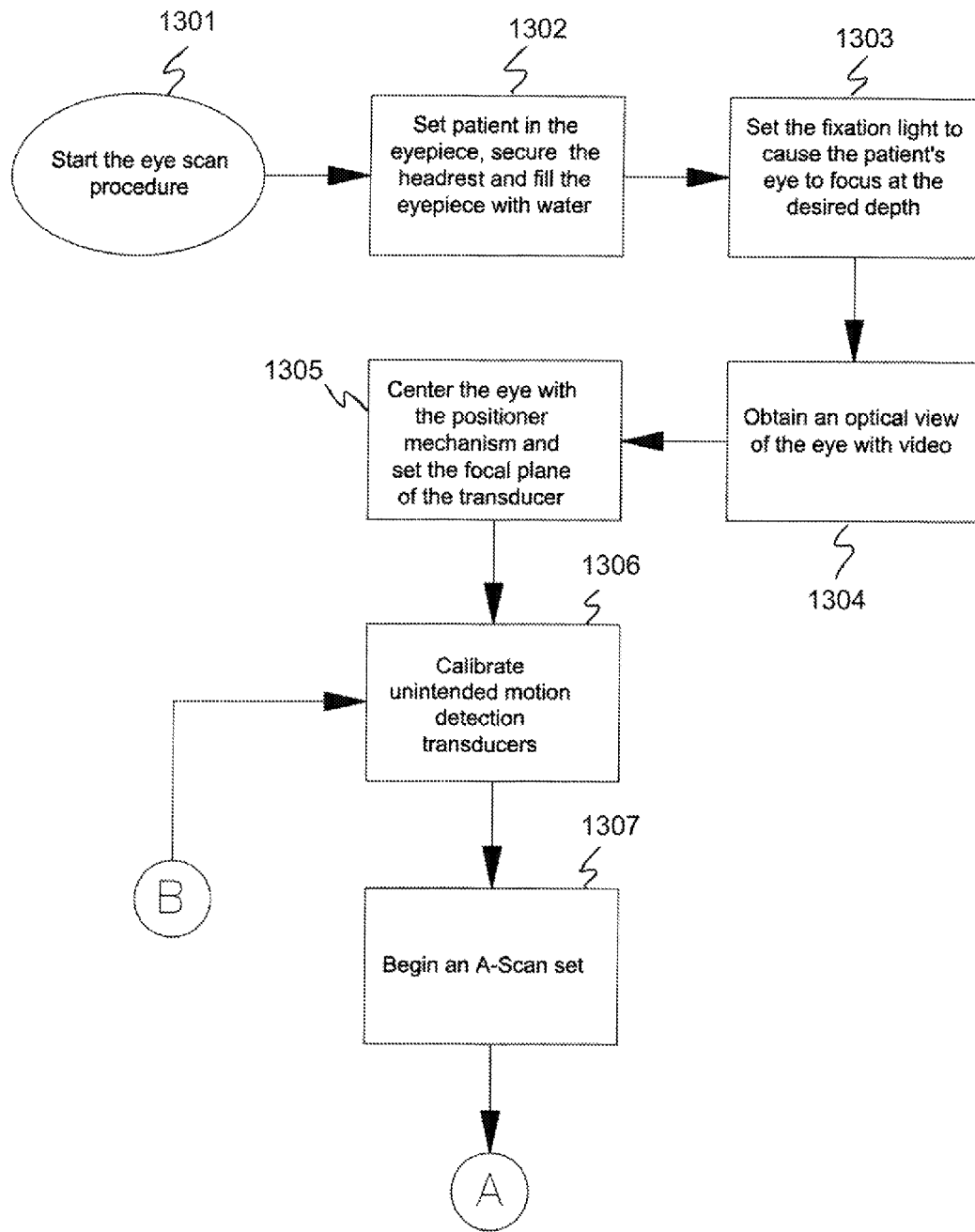
FIGS. 13a and 13b show a flow chart of a corrective ultrasound tracking system.
Figure 13B:
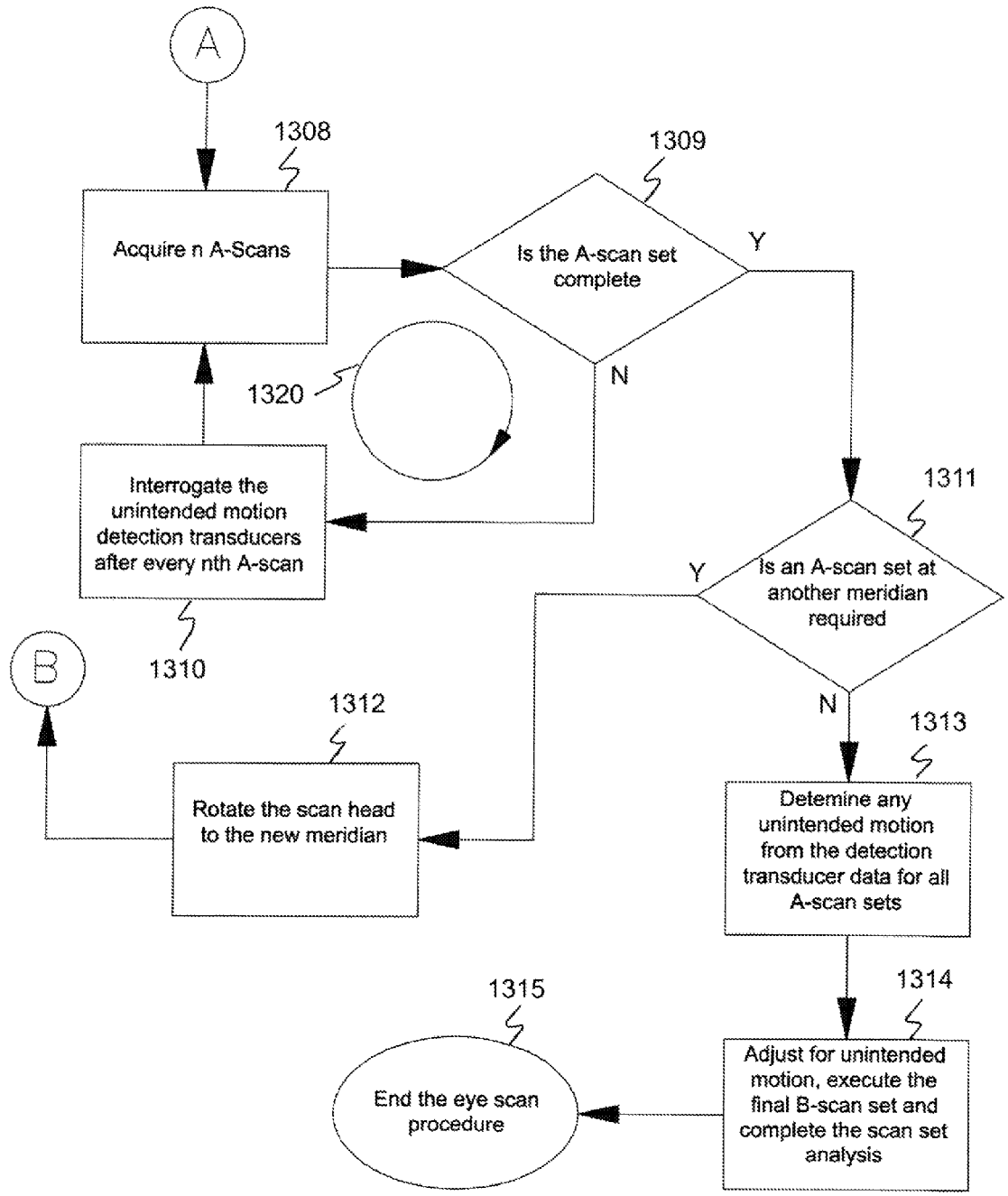

FIGS. 13a and 13b show a flow chart of a corrective ultrasound tracking system. A scan procedure 1301 begins with the patient sitting, placing their head in a headrest such as shown in FIG. 5 and then placing the eye to be scanned in an eyepiece such as shown in FIG. 6. This firmly fixes the patient's head and eye socket with respect to the scan machine. The procedure proceeds as described in FIGS. 12a and 12b through step 1307 where acquisition of the first A-set begins. As shown in step 1308, n A-scans are acquired (where n is a number between about 10 and about 20). After every nth A-scan, if the A-scan set is not complete (step 1309), then the unintended motion detection transducers are interrogated in step 1310 to acquire data on any motion of their anchor points or fitted surface. As can be seen, the acquisition of A-scans and unintended motion calibration is continued as indicated by logic loop 1320. If the A-scan set is complete (step 1309) then if another A-scan set is required at a different meridian (step 1311), then the scan head is rotated by the positioner to the new meridian in step 1312 and the program is directed back to step 1306 to begin re-calibration of the unintended motion detection transducers. If another A-scan set is not required at a different meridian, then the scanning is complete and the computer automatically advances in step 1313 to determine the trajectory of unintended motion by analyzing the data from the unintended motion detection transducers. The program proceeds to step 1314 to perform the analysis of the A-scans, adjust for any unintended motion and the construction of the desired B-scans (that is, the final ultrasound images). Then the eye scan procedure is completed (step 1315). At this point the water in the eye seal is drained and the patient is free to leave or undergo another eye scan procedure on their other eye.

The procedure described in FIG. 13 may be applied when unintended motion is detected and characterized and is useful for correcting the A-scan data for the unintended motion. In this case, the procedure is need not be aborted due to unintended motion of the eye.

Since the patient is sitting with their head in a headrest and their eye to be scanned resting in an eyepiece, the expected unintended motion is mainly due to involuntary rotational motion of the eye in its orbit. Some unintended z-motion may be expected due to the compliance of the eye seal material in contact with the patient's eye socket. Very little x- or y-motion is expected because the patient's head is fixed by the head rest and the patient's eye socket is fixed by the eye seal. Thus, the unintended motion detection transducers are designed and placed to best detect any rotational motion of the eye in its orbit. If there is unintended z-motion, then all the unintended motion detection transducers would be expected to show the same amount of displacement.

Figure 14:
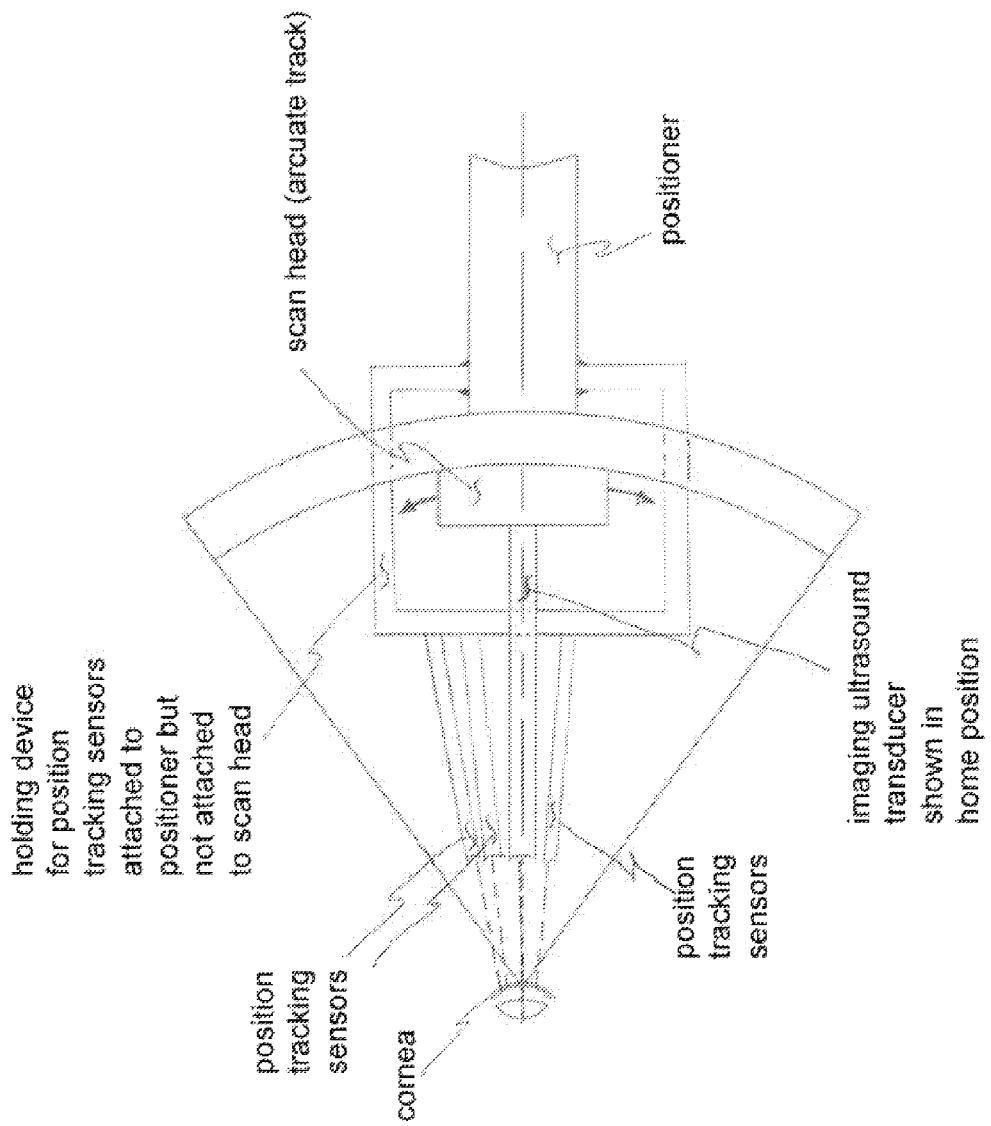
FIG. 14 is a schematic of the main elements of an alternate motion tracking scanning system.

FIG. 14 illustrates alternate locations for tracking sensors where the tracking sensors are positioned on a frame or holding device which is attached to the positioning mechanism. This configuration locates the tracking sensors closer to the eye than the configuration of FIG. 8 and therefore its tracking transducers require less signal power than the transducers of FIG. 8. These tracking transducers may therefore be higher frequency than the transducers of FIG. 8 and be capable of resolving smaller time intervals and therefore may be able to track smaller unintended rotational movements of the eyeball. These tracking transducers may also be positioned closer to normal to the surface of the cornea.

In yet another embodiment, the disclosed systems and methods may be partially implemented in software that can be stored on a storage medium to include a computer-readable medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

In one embodiment, one or more computers are used to control, among other things, the scan head assembly and/or the ultrasound transducer and/or the position sensor(s). In one embodiment, the user interacts with the computer through any means known to those skilled in the art, to include a keyboard and/or display to include a touch-screen display. The term "computer-readable medium" as used herein refers to any tangible storage and/or transmission medium that participate in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

The disclosure has been described with reference to the preferred embodiments. Modifications and alterations will occur to others upon a reading and understanding of the preceding detailed description. It is intended that the disclosure be construed as including all such modifications and alterations insofar as they come within the scope of the appended claims or the equivalents thereof.

A number of variations and modifications of the disclosures can be used. As will be appreciated, it would be possible to provide for some features of the disclosures without providing others.

The present disclosure, in various embodiments, includes components, methods, processes, systems and/or apparatus substantially as depicted and described herein, including various embodiments, sub-combinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, for example for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover though the description of the disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. An ultrasonic scanning system, comprising:
   an instrument body to engage a patient and position a head and an eye of the patient; and
   a positioner assembly connected to the instrument body, the positioner assembly comprising a scan head assembly, which comprises at least one guide track, at least one transducer carriage and at least one ultrasound transducer, wherein the at least one transducer carriage moves along the at least one guide track;
   wherein the at least one ultrasound transducer is mounted on the at least one transducer carriage, and the at least one ultrasound transducer emits an ultrasound pulse and receives an ultrasound pulse reflected from one or more components of the patient's eye when the patient is engaged with the instrument body; and
   at least one ultrasound position sensor fixed relative to the positioner assembly, wherein the at least one ultrasound position sensor measures a position of the patient's eye relative to at least one of an eye socket, the instrument body, and the positioner assembly using an eye fiducial, wherein a computer processor is configured to alter, using the measurement of the position of the patient's eye, a recorded position in a coordinate system of individual ultrasound pulses in the received ultrasound pulses reflected from the one or more components of the patient's eye to account for movement of the patient's eye during ultrasound pulse emission and/or reception, and wherein the computer processor is configured to construct an ultrasound image of the patient's eye based on the received ultrasound pulses and the corresponding, altered positions in the coordinate system.

2. The system of claim 1, wherein the instrument body further comprises an eyepiece member to engage the patient and adapted to urge positional fixing of an eye socket of the patient's eye.

3. The system of claim 2, wherein the instrument body further comprises a headrest member to engage a non-planar portion of the patient.

4. The system of claim 1, wherein the patient is adapted to be fixed relative to the instrument body such that an eye socket of the patient's eye is substantially fixed relative to the instrument body.

5. The system of claim 1, wherein the eye fiducial is an anterior surface of a cornea, a posterior surface of a cornea, a posterior apex of a lens, a pole of a lens, an anterior surface of a lens, a posterior surface of a lens, an inside edge of an iris that defines a pupil or a posterior pigment layer of an iris.

6. The system of claim 1, wherein the at least one ultrasound position sensor is a plurality of ultrasound position sensors that are interconnected to a holding device, which is interconnected to the instrument body.

7. The system of claim 1, wherein the at least one transducer carriage moves along at least one guide track under computer control.

8. The system of claim 1, wherein the ultrasound pulses of the at least one ultrasound transducer and the measurements of the position of the patient's eye are recorded on a non-transitory computer readable medium.

9. The system of claim 1, wherein the at least one ultrasound position sensor continuously measures the position of the patient's eye.

10. The system of claim 1, wherein the at least one ultrasound position sensor measures the position of the patient's eye relative to an operator-selected threshold.

11. A method of forming an ultrasound image of a patient's eye corrected for eye movement, comprising:
(a) positioning a patient to engage an ultrasonic scanning system, the ultrasonic scanning system comprising: an instrument body configured to engage the patient and position a head and an eye of the patient; and a positioner assembly connected to the instrument body, the positioner assembly comprising a scan head assembly and at least one ultrasound position sensor fixed relative to the positioner assembly, the scan head assembly comprising at least one guide track, at least one transducer carriage and at least one ultrasound transducer, and wherein the at least one transducer carriage moves along the at least one guide track;
(b) moving the at least one ultrasound transducer along the at least one guide track while emitting an ultrasound pulse and receiving an ultrasound pulse reflected from one or more components of the patient's eye;
(c) measuring a position of the patient's eye, by the at least one ultrasound position sensor, relative to at least one of an eye socket, the instrument body, and the positioner assembly using an eye fiducial;
(d) recording the ultrasound pulses from the at least one ultrasound transducer that are reflected from the one or more components of the patient's eye on a non-transitory computer readable medium, the recorded ultrasound pulses having a recorded position in a common global coordinate system;
(e) recording the position of the patient's eye from the at least one ultrasound position sensor on a non-transitory computer readable medium;
(f) based on the measurement of the position of the patient's eye, altering the recorded position in the common global coordinate system of individual ultrasound pulses in the ultrasound pulses reflected from the one or more components of the patient's eye to correct for movement of the patient's eye during ultrasound pulse emission and/or reception; and
(g) constructing an ultrasound image of the patient's eye based on the recorded ultrasound pulses and corresponding, altered positions in the common global coordinate system.

12. The method of claim 11, wherein the instrument body further comprises an eyepiece engaging the patient and urging positional fixing of an eye socket of the patient's eye.

13. The method of claim 12, wherein the instrument body further comprises a headrest engaging a non-planar portion of the patient and further urging positional fixing of the eye socket.

14. The method of claim 11, wherein the at least one ultrasound position sensor is a plurality of ultrasound position sensors and the at least one transducer carriage automatically moves along the at least one guide track under computer control.

15. The method of claim 11, further comprising:
(h) redoing at least one of steps (b)-(e), if the measurements of the patient's eye exceeds an operator-selected threshold.

16. The method of claim 15, further comprising:
(i) emitting and receiving a second set of ultrasound pulses reflected from one or more components of the patient's eye, if the measurements of the patient's eye does not exceed the operator-selected threshold.

* * * * *